United States Patent
Takahashi et al.

(10) Patent No.: US 12,331,280 B2
(45) Date of Patent: Jun. 17, 2025

(54) CELL CULTURE DEVICE, METHOD FOR CULTURING CELLS, AND METHOD FOR PRODUCING PRODUCT

(71) Applicant: FUJIFILM Corporation, Tokyo (JP)

(72) Inventors: Naoto Takahashi, Kanagawa (JP); Shinichi Nakai, Kanagawa (JP); Hiroshi Sakuyama, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 961 days.

(21) Appl. No.: 17/387,091

(22) Filed: Jul. 28, 2021

(65) Prior Publication Data

US 2021/0355430 A1   Nov. 18, 2021

Related U.S. Application Data

(63) Continuation of application No. PCT/JP2020/001094, filed on Jan. 15, 2020.

(30) Foreign Application Priority Data

Feb. 4, 2019  (JP) ................... 2019-018245

(51) Int. Cl.
  *C12N 1/02*  (2006.01)
  *C12M 1/00*  (2006.01)
  (Continued)

(52) U.S. Cl.
  CPC ............ *C12N 1/02* (2013.01); *C12M 29/00* (2013.01); *C12N 5/0682* (2013.01); *F04B 43/0054* (2013.01)

(58) Field of Classification Search
  None
  See application file for complete search history.

(56) References Cited

U.S. PATENT DOCUMENTS 4,864,918 A * 9/1989 Martin ................ F04B 43/0054
                                            92/103 SD
6,158,327 A * 12/2000 Huss .................. F04B 43/0063
                                            92/100
(Continued)

FOREIGN PATENT DOCUMENTS

FR   2 566 846 A1    1/1986
FR   2566846    *    1/1986
(Continued)

OTHER PUBLICATIONS

Song. ("Novel Model for Uniaxial Strain-Rate-Dependent Stress-Strain Behavior of Ethylene-Propylene-Diene Monomer Rubber in Compression or Tension"). (Year: 2004).*
(Continued)

*Primary Examiner* — Holly Kipouros
*Assistant Examiner* — Nathan G Esperon
(74) *Attorney, Agent, or Firm* — Birch, Stewart, Kolasch & Birch, LLP

(57) ABSTRACT

In the cell culture device, a volume of a space defined by a diaphragm of the diaphragm pump and a plane at an outer edge of the diaphragm is 1 cm³ or more and 20 cm³ or less, in a case where an angle formed by a straight line connecting a foot of a perpendicular line from the apex to the plane to each point in the diaphragm and by the perpendicular line is denoted by an angle A, a thickness H of the diaphragm is within a range of 0.5 mm or more and 1.5 mm or less where the angle A is from 0° to 75°, and in a case where a thickness of the diaphragm at the apex is denoted by $H_T$, the thickness H satisfies a relationship of $1 \le H_T/H \le 1.75$ at any point where the angle A is from 0° to 75°.

14 Claims, 6 Drawing Sheets

(51) Int. Cl.
    *C12N 5/071*     (2010.01)
    *F04B 43/00*     (2006.01)

(56) References Cited

U.S. PATENT DOCUMENTS

| | | | |
|---|---|---|---|
| 6,544,424 B1 * | 4/2003 | Shevitz | C12M 47/02 |
| | | | 210/636 |
| 7,779,746 B1 | 8/2010 | Eiermann | |
| 2005/0074340 A1 * | 4/2005 | Xu | F04B 43/06 |
| | | | 417/395 |
| 2008/0077068 A1 | 3/2008 | Orr | |
| 2008/0216898 A1 * | 9/2008 | Grant | A61M 1/15625 |
| | | | 137/154 |
| 2014/0199193 A1 * | 7/2014 | Wilt | A61M 1/341 |
| | | | 417/474 |
| 2015/0289501 A1 * | 10/2015 | Raredon | C12M 21/08 |
| | | | 435/284.1 |
| 2017/0102383 A1 | 4/2017 | Miyamoto et al. | |
| 2018/0238317 A1 * | 8/2018 | Ward | A63B 21/156 |
| 2019/0201820 A1 * | 7/2019 | Pavlik | F04B 53/20 |
| 2019/0338230 A1 * | 11/2019 | Bhushan | C12M 21/08 |
| 2021/0261900 A1 * | 8/2021 | Bhargav | B01D 65/02 |
| 2022/0088538 A1 * | 3/2022 | Pavlik | F04B 23/06 |

FOREIGN PATENT DOCUMENTS

| | | | | |
|---|---|---|---|---|
| JP | 2010-29109 A | 2/2010 | | |
| JP | 2012-147678 A | 8/2012 | | |
| WO | WO-0233052 A2 * | 4/2002 | ............ | C12M 21/08 |
| WO | WO-2005067498 A2 * | 7/2005 | ............ | C12M 23/26 |
| WO | WO 2016/002847 A1 | 1/2016 | | |

OTHER PUBLICATIONS

Japanese Notice of Reasons for Refusal for Japanese Application No. 2020-571060, dated Jul. 5, 2022, with an English translation.
International Preliminary Report on Patentability and Written Opinion of the International Searching Authority for International Application No. PCT/JP2020/001094, dated Aug. 19, 2021, with an English translation.
International Search Report for International Application No. PCT/JP2020/001094, dated Apr. 7, 2020, with an English translation.
Extended European Search Report for European Application No. 20752524.7, dated Mar. 3, 2022.
Japanese Notice of Reasons for Refusal for Japanese Application No. 2020-571060, dated Dec. 6, 2022, with an English translation.
Singapore Office Action for Singaporean Application No. 11202108093U, dated Nov. 4, 2022.

\* cited by examiner

B: PARTIALLY DISCOLORED AFTER USE

D: TORN DURING USE

A: NOT TORN, CRACKED, AND DISCOLORED AFTER USE

C: PARTIALLY CRACKED AFTER USE

CELL CULTURE DEVICE, METHOD FOR CULTURING CELLS, AND METHOD FOR PRODUCING PRODUCT

CROSS-REFERENCE TO RELATED APPLICATIONS

This application is a continuation application of International Application No. PCT/JP2020/001094 filed Jan. 15, 2020 the disclosure of which is incorporated herein by reference in its entirety. Further, this application claims priority from Japanese Patent Application No. 2019-018245, filed Feb. 4, 2019, the disclosure of which is incorporated herein by reference in its entirety.

BACKGROUND

Technical Field

The present disclosure relates to a method for culturing cells, a method for producing a product, and a cell culture device.

Related Art

In a case of culturing cells, a culture solution may be extracted for various purposes from the culture vessel using a pump. For example, in JP2010-29109A, a culture solution is extracted from the culture vessel for the intended purpose of capturing microorganisms that contaminate the culture solution.

U.S. Pat. No. 6,544,424B describes that a culture solution extracted from the culture vessel is filtered by a tangential flow type method using a diaphragm pump.

SUMMARY

An object of the present invention is to provide a cell culture device and a method for culturing cells, with which both good cell proliferation properties and the suppression of diaphragm damage can be achieved in a case where a cell suspension is extracted with a diaphragm pump having a small capacity, and a method for producing a product using the method for culturing cells.

The means for solving the above problems includes the following aspects.

<1> A cell culture device including:
a culture vessel containing a cell suspension; and
a diaphragm pump for extracting the cell suspension from the culture vessel,
in which a volume of a space defined by a diaphragm of the diaphragm pump and a plane F including a surface of an outer edge part of the diaphragm on a side far from an apex of the diaphragm is 1 cm³ or more and 20 cm³ or less,
in a case where an angle formed by a straight line connecting a foot of a perpendicular line which is drawn from the apex of the diaphragm to the plane F to each point in the diaphragm and by the perpendicular line is denoted by an angle A at each point, a thickness H of the diaphragm is within a range of 0.5 mm or more and 1.5 mm or less at any point in a region where the angle A is from 0° to 75°, and
in a case where a thickness of the diaphragm at the apex of the diaphragm is denoted by $H_T$, the thickness H of the diaphragm satisfies Expression 1 at any point in the region where the angle A is from 0° to 75°, $1 \le H_T/H \le 1.75$ (Expression 1).

<6> A method for culturing cells, including:
culturing cells in a cell suspension contained in a culture vessel; and
extracting the cell suspension from the culture vessel with a diaphragm pump,
in which a volume of a space defined by a diaphragm of the diaphragm pump and a plane F including a surface of an outer edge part of the diaphragm on a side far from an apex of the diaphragm is 1 cm³ or more and 20 cm³ or less,
in a case where an angle formed by a straight line connecting a foot of a perpendicular line which is drawn from the apex of the diaphragm to the plane F to each point in the diaphragm and by the perpendicular line is denoted by an angle A at each point, a thickness H of the diaphragm is within a range of 0.5 mm or more and 1.5 mm or less at any point in a region where the angle A is from 0° to 75°, and
in a case where a thickness of the diaphragm at the apex of the diaphragm is denoted by $H_T$, the thickness H of the diaphragm satisfies Expression 1 at any point in the region where the angle A is from 0° to 75°, $1 \le H_T/H \le 1.75$ (Expression 1).

DETAILED DESCRIPTION

Figure 1:
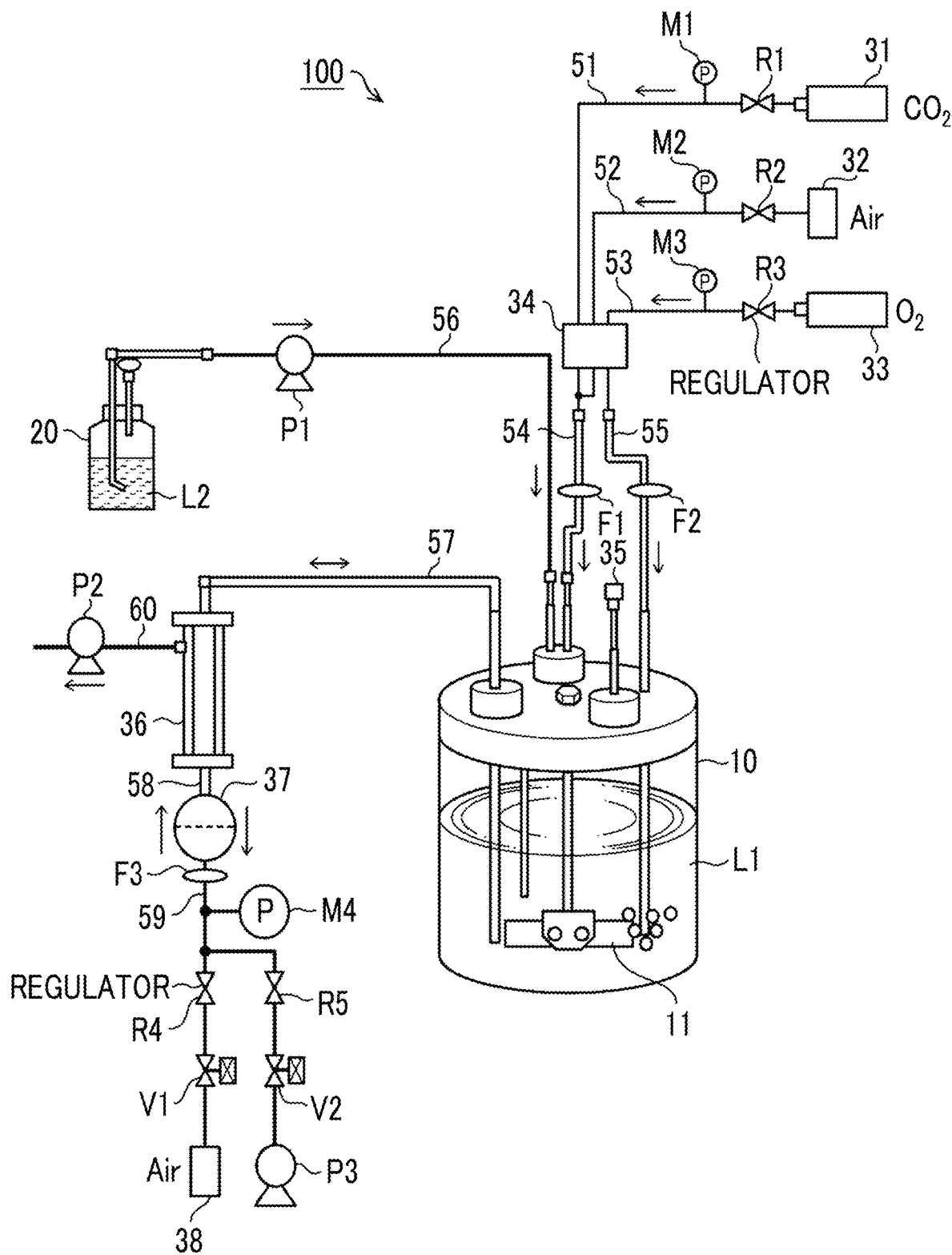
FIG. 1 is a view illustrating an example of a configuration of a cell culture device according to the present disclosure.

Hereinafter, a cell culture device, a method for culturing cells, and a method for producing a product, according to the present disclosure, will be described. However, the embodiments according to the present disclosure are not limited to the following embodiments and can be implemented with appropriate modifications.

In the present disclosure, the numerical range represented by using "to" means a range including the numerical values before and after "to" as the minimum value and the maximum value, respectively.

In a numerical range described in a stepwise manner in the present disclosure, an upper limit value or a lower limit value described in a certain numerical range may be replaced with an upper limit value or a lower limit value of another numerical range described in a stepwise manner. Further, in the numerical ranges described in the present disclosure, the upper limit value or the lower limit value of a numerical range may be replaced with the value shown in Examples.

In the present disclosure, a combination of two or more preferred aspects is a more preferred aspect.

In the present disclosure, in a case where there are a plurality of substances corresponding to each of components, unless otherwise particularly specified, the amount of each of components means the total amount of the plurality of substances.

In the present disclosure, the term "process" includes not only an independent process but also a process that cannot be clearly distinguished from other processes, as long as the intended purpose of the process is achieved.

The cell culture device according to the present disclosure is a cell culture device that includes:
 a culture vessel containing a cell suspension; and
 a diaphragm pump for extracting the cell suspension from the culture vessel,
 in which a volume of a space defined by a diaphragm of the diaphragm pump and a plane F including a surface of an outer edge part of the diaphragm on a side far from an apex of the diaphragm is 1 cm³ or more and 20 cm³ or less, and
 in a case where an angle formed by a straight line connecting a foot of a perpendicular line which is drawn from the apex of the diaphragm to the plane F to each point in the diaphragm and by the perpendicular line is denoted by an angle A at each point, a thickness H of the diaphragm is within a range of 0.5 mm or more and 1.5 mm or less at any point in a region where the angle A is from 0° to 75°, and
 in a case where a thickness of the diaphragm at the apex of the diaphragm is denoted by $H_T$, the thickness H of the diaphragm satisfies Expression 1 at any point in the region where the angle A is from 0° to 75°.

$$1 \leq H_T/H \leq 1.75 \qquad \text{(Expression 1)}$$

In cell culture, a pump may be used for the intended purpose of extracting a culture solution from the culture vessel. Although it is conceivable to use a diaphragm pump for this purpose, the conventional diaphragm pump for cell culture is a diaphragm pump having a relatively large capacity, and there has been no case where a small diaphragm pump in which the volume of the space defined by a diaphragm (described later) is, for example, 20 cm³ or less, was used for cell culture. On the other hand, for example, in experimental culture, it is not intended to obtain a large number of cells or a large amount of a product, and thus, the inventors of the present invention considered that it is preferable to reduce a culture scale from the viewpoint of cost reduction such as the reduction of the use of a medium. The inventors of the present invention also considered reducing the size of the diaphragm pump in association with the reduction of the culture scale. However, the inventors of the present invention found that in a case where the size of the diaphragm pump is simply reduced, the thickness of the diaphragm is also decreased, and as a result, the strength of the diaphragm is reduced, and the diaphragm is damaged during the culture.

On the other hand, the inventors of the present invention found that in a case where the thickness of the diaphragm is increased in order to secure the strength of the small diaphragm, cells may receive stress by the impact at the time of reversing the diaphragm, which adversely affects the proliferation properties of the cells.

Then, the inventors of the present invention have found that in a case where the thickness distribution in the diaphragm is specifically designed, it is possible to achieve suppression of diaphragm damage while ensuring cell proliferation properties, whereby the cell culture device, the method for culturing cells, and the method for producing a product, according to the present disclosure, have been invented.

In the cell culture device according to the present disclosure, the culture vessel can be a culture vessel such as a culture vessel (also referred to as a bioreactor) of a general culture device or a suitable container other than this. Examples of the culture device include a fermenter type tank culture device, an air lift type culture device, a culture flask type culture device, a spinner flask type culture device, a microcarrier type culture device, a fluidized bed type culture device, a hollow fiber type culture device, a roller bottle type culture device, and a filled-tank type culture device.

Figure 2:
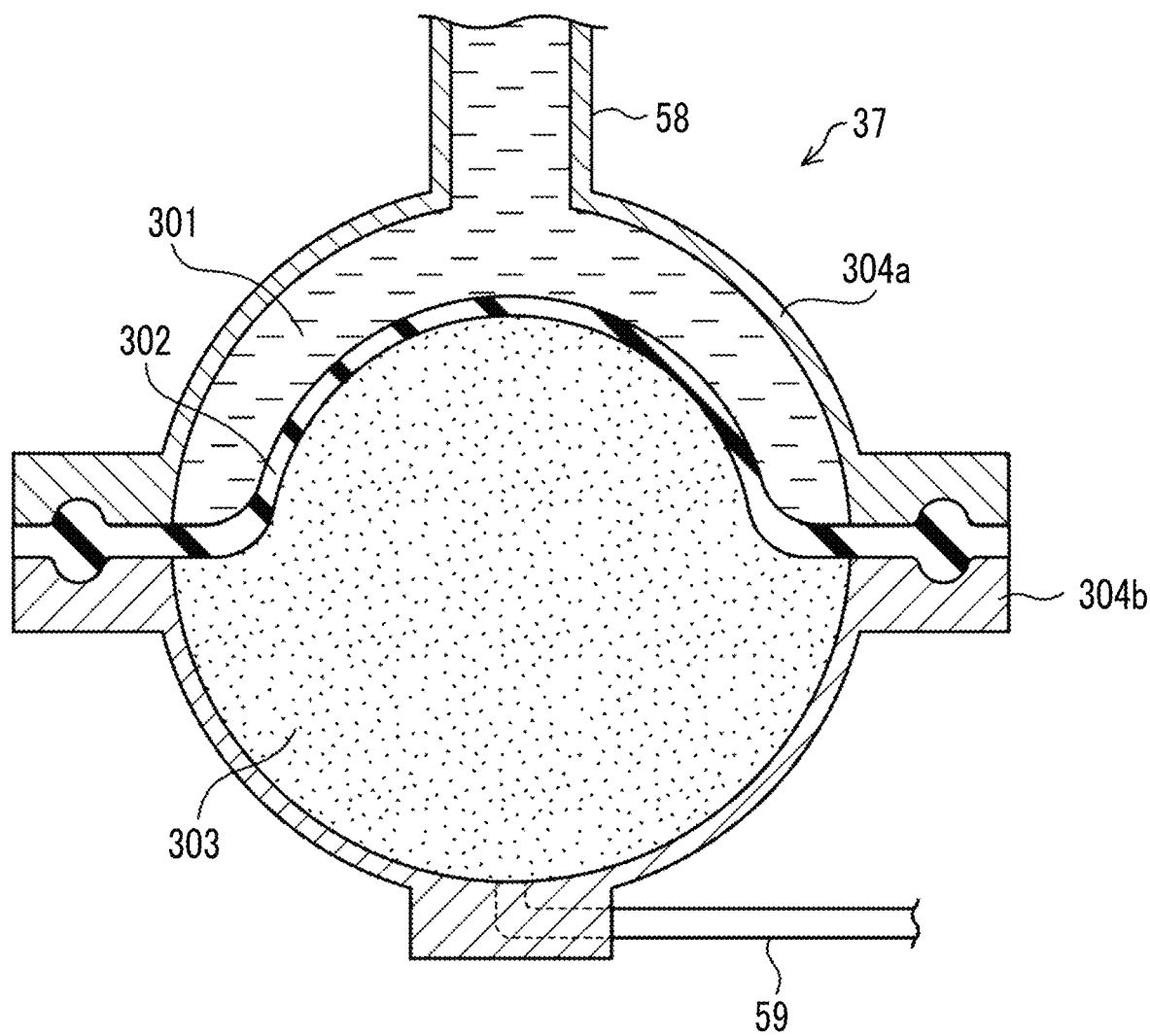
FIG. 2 is a view illustrating an example of a configuration of a diaphragm pump in the cell culture device according to the present disclosure.

The diaphragm pump is a pump that sucks and discharges a liquid by a reciprocating motion of a barrier membrane called a diaphragm. In FIG. 2, a typical example of a diaphragm pump that can be used in the cell culture device according to the present disclosure is illustrated. The diaphragm pump illustrated in FIG. 2 is a reciprocating flow generation type diaphragm pump that does not have a check valve; however, the diaphragm pump that can be used in the cell culture device according to the present disclosure is not limited to this and may be a diaphragm pump having a check valve to be capable of forming a unidirectional flow.

FIG. 2 is a cross-sectional view illustrating a cross section of a diaphragm pump 37. The diaphragm pump 37 illustrated in FIG. 2 is connected to a flow path (a pipe) 58 through which a liquid flows and a flow path (a tube) 59 through which a gas flows. The diaphragm pump 37 has a housing consisting of a portion 304a and a portion 304b, and a diaphragm 302, and both end parts of the diaphragm 302 are fixed in the portion 304b of the housing. As a result, both end parts of the diaphragm 302 housed in the portion 304b of the housing do not move even in a case where the diaphragm pump is in operation. These both end parts actually form an outer edge (an outer circumference) in the radial direction of the diaphragm and are an annular outer edge part. The housing consisting of the portion 304a and the portion 304b may be made of any material having the strength required for the diaphragm pump, such as iron, stainless steel, and plastic.

The diaphragm 302 divides the space inside the diaphragm pump 37 into two chambers, a chamber 301 and a chamber 303. The chamber 301 is filled with a liquid from the flow path 58, and the chamber 303 is filled with a gas from the flow path 59. In a case where the inside of the flow path 59 is depressurized by a vacuum pump or the like, the pressure inside the chamber 303 is also decreased, and thus the diaphragm 302 has a shape of an arc drawn toward the chamber 303 side due to the pressure difference between the chamber 301 and the chamber 303. On the other hand, in a case where the inside of the flow path 59 is pressurized by a pressurized gas source or the like, the pressure inside the chamber 303 is also increased, and thus the diaphragm 302 has a shape of an arc drawn toward the chamber 301 side due to the pressure difference between the chamber 301 and the chamber 303. A reciprocating flow can be generated in the flow path 58 by reciprocating between these two states. Such a reciprocating flow can be used for filtration by a tangential flow filtration method or the like.

On the other hand, as described above, it is also possible to form a unidirectional flow by the diaphragm pump. In this case, it is possible to form a unidirectional flow due to the reciprocation (the reversal) of the diaphragm 302 by installing another flow path in addition to the flow path 58 in the chamber 301 and installing a check valve to each of the flow paths.

As illustrated in FIG. 2, the center of the diaphragm is the point farthest from the plane including the lower surface of the annulus of the outer edge part of the diaphragm in FIG. 2 and can be referred to as the apex of the diaphragm. This is because the center of the diaphragm is located at the apex part of the arc formed by the diaphragm in a case of being viewed in the cross section as illustrated in FIG. 2.

Since the diaphragm repeats reciprocation as described above, it is preferably an elastic body. The elastic body refers to a member that deforms in a case where a force is applied and returns to an original shape thereof in a case where the force is removed, and in particular, refers to a member made of a material having rubber elasticity. The rubber elasticity refers to an elasticity having a smaller modulus of elasticity than that of a metal and a large displacement magnitude with respect to a force, has a modulus of elasticity (a Young's modulus) of about one digit of MPa to three digits of MPa at 25° C., and specifically refers to an elasticity of about 1 MPa to 60 MPa. The Young's modulus can be measured, for example, using "TGI 100 kN" (trade name) (manufactured by MinebeaMitsumi Inc.) and a method in accordance with JIS K7161 (2014) (test piece dimensions: length 5 cm×width 1.5 cm×thickness 0.1 cm, test speed: 0.5 mm/min).

In the cell culture device according to the present disclosure, the volume of a space defined by a diaphragm and a plane F including a surface of an outer edge part of the diaphragm on a side far from an apex of the diaphragm is 1 $cm^3$ or more and 20 $cm^3$ or less, in a case where an angle formed by a straight line connecting a foot of a perpendicular line which is drawn from the apex of the diaphragm to the plane F to each point in the diaphragm and by the perpendicular line is denoted by an angle A at each point, a thickness H of the diaphragm is within a range of 0.5 mm or more and 1.5 mm or less at any point in a region where the angle A is from 0° to 75°, and in a case where a thickness of the diaphragm at the apex of the diaphragm is denoted by $H_T$, the thickness H of the diaphragm satisfies Expression 1 at any point in the region where the angle A is from 0° to 75°.

$1 \leq H_T/H \leq 1.75$ (Expression 1)

In the present disclosure, the various regions of the diaphragm, the volume of the space, the thicknesses at a point of the diaphragm are explained; however, the region of the diaphragm, the volume of the space, and the thickness at the point in the present disclosure in all the descriptions thereof means a region of the diaphragm, a volume of the space, and a thickness at the point measured in a state in which external pressure is not applied to the diaphragm (the elastic body constituting the diaphragm) unless otherwise particularly specified. During the operation of the diaphragm pump, a pressure difference is generated between the pressures applied to both surfaces of the diaphragm, whereby the diaphragm repeats a movement such as reversal. However, the region of the diaphragm, the volume of the space, and the thickness at the point which are described in the present disclosure are not measured in a state in which such a pressure difference is present, that is, a state in which pressure is applied from any one surface of the diaphragm, but are a region of the diaphragm, a volume of the space, and a thickness at the point which are measured in a state in which external pressure is not applied, for example, by taking out the diaphragm from the diaphragm pump. In a case where a diaphragm is placed on a support base to measure thickness, the diaphragm receives its weight in the different direction depending on the placement direction; however, the deformation due to the diaphragm's own weight is negligible and thus not particularly on the measurement of the region, the volume of the space, and the thickness.

Figure 3A:
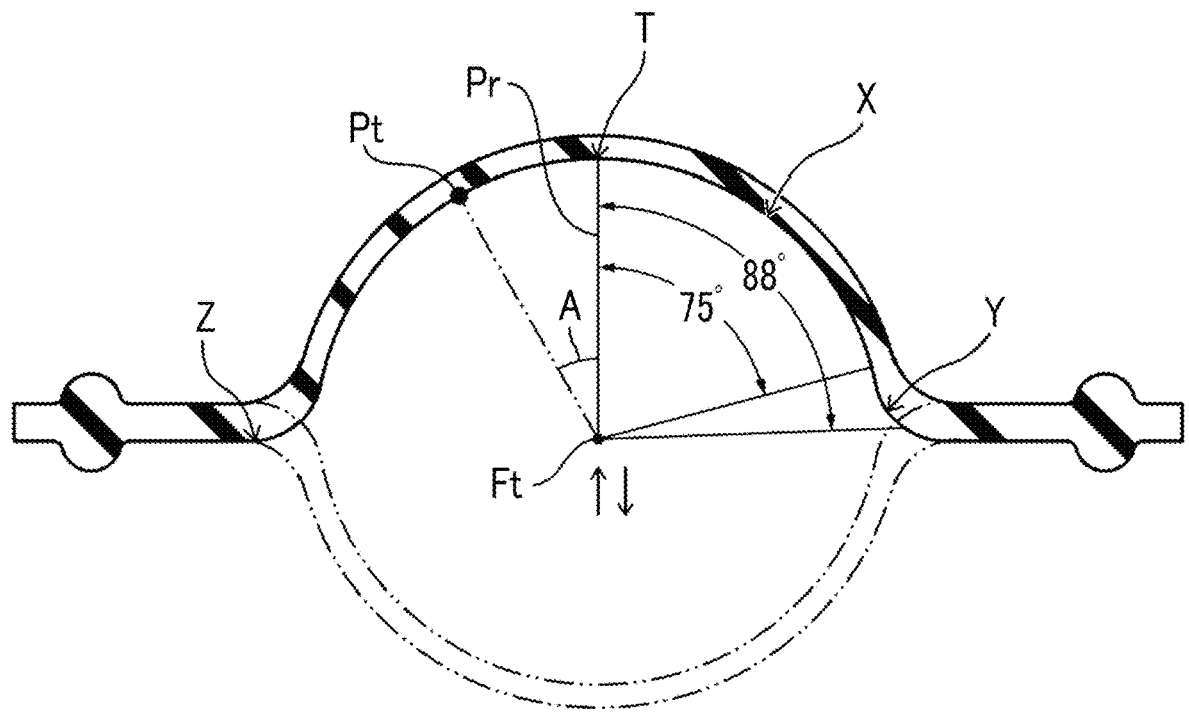
FIG. 3A is a view for explaining an angle A at each point on a diaphragm.
Figure 3B:
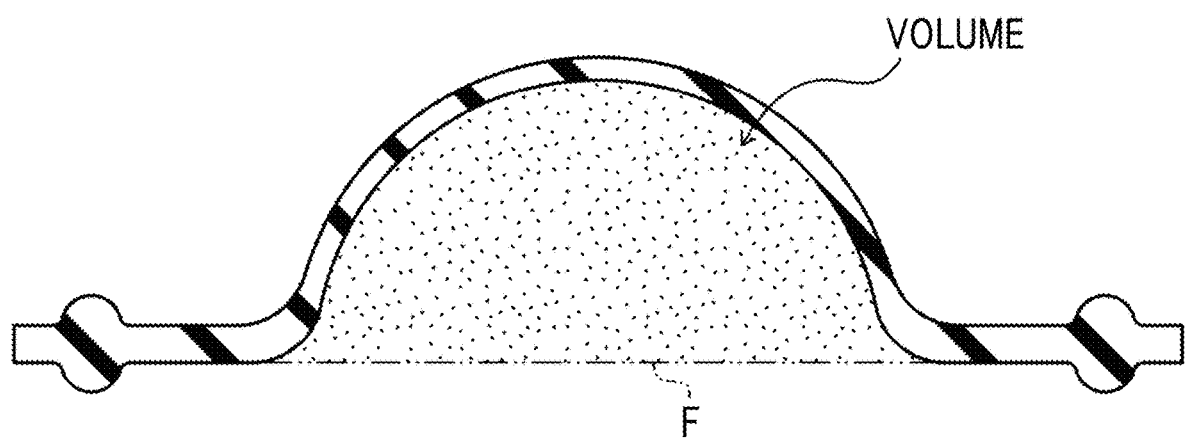
FIG. 3B is a view for explaining a volume defined by the diaphragm.

The above space and the above angle A will be described with reference to FIG. 3A and FIG. 3B. As illustrated in FIG. 3A and FIG. 3B, the diaphragm has an outer edge part that is flat and annular except for a protruding part for strengthening the fixing to the housing, and a movable part having a dome shape, which is bulged from the outer edge part. For this reason, the center of the diaphragm is an apex T of the dome-shaped bulge shape. As described in FIG. 2, the movable part can be reversed due to the pressure difference between the chambers partitioned by the diaphragm. In FIG. 3A and FIG. 3B, the outer edge part of the diaphragm is fixed to the housing of the diaphragm pump, and the lower surface (a first surface) of the outer edge part in FIG. 3A and FIG. 3B belongs to the same plane except for the protruding part for strengthening the fixing to the housing. This lower surface actually has an annular shape. Like the lower surface, the upper surface (a second surface) of the outer edge part in FIG. 3A and FIG. 3B also has an annular shape and also belongs to the same plane except for the protruding part for strengthening the fixing to the housing. The plane including the lower surface (excluding the protruding part) of the outer edge part of the diaphragm in FIG. 3A and FIG. 3B is referred to as a plane F in the present disclosure. The plane F is a virtual plane formed by extending the plane to which the lower surface of the outer edge part of the diaphragm belongs, to the space under the movable part. The lower surface of the outer edge part in FIG. 3A and FIG. 3B is a surface of surfaces of the outer edge part on the side far from the apex T (that is, the center point) of the diaphragm. In other words, in FIG. 3A, since the apex T is a point in a region bulged upward from the outer edge part, the surface farther from the apex T among the lower surface and the upper surface of the outer edge part is the lower surface.

In a case where the diaphragm is reversed from the apex T, the diaphragm has a shape shown by the virtual line in FIG. 3A; however, even in this case, since the shape itself is the same and only the direction of the arc drawn is reversed, the case of the shape illustrated by the solid line FIG. 3A will be described.

The "space defined by a diaphragm and a plane F including a surface of an outer edge part of the diaphragm on a side far from an apex of the diaphragm" refers to a closed space defined (surrounded) by the lower surface (the surface closer to the plane F) of the arc-shaped portion of the diaphragm in FIG. 3B and by the plane F. The cross section of this closed space is illustrated as a stippled part in FIG. 3B. The volume of this closed space is a value of about ½ of the volume change of the liquid side chamber (the chamber 301 in FIG. 2), where the volume change is caused by reversing the diaphragm, and is an index of the amount of liquid flows into or discharged from the diaphragm pump. In the diaphragm pump of the present disclosure, the volume of the closed space is 1 $cm^3$ or more and 20 $cm^3$ or less, which is smaller than the volume of the diaphragm pump that has been conventionally used for culture.

In a case where the volume of a space defined by a diaphragm and a plane F including a surface of an outer edge part of the diaphragm on a side far from an apex of the diaphragm is 1 $cm^3$ or more, a sufficient amount of cell suspension can be extracted from the culture vessel. In particular, in a case where a diaphragm pump is used to remove waste products or the like in the medium in perfusion culture, the waste products of cells can be sufficiently discharged to the outside of the system by filtration or the like, and the proliferation properties of the cells are improved, whereby the cell survival rate is easily maintained. Further, in a case where the volume of a space defined by a diaphragm and a plane F including a surface of an outer edge part of the diaphragm on a side far from an apex of the diaphragm is 20 cm$^3$ or less, it can be easily avoided the retention time of the culture solution outside the cell container becomes excessively long. Since the outside of the cell container is a place under conditions in which oxygen supply, temperature maintenance, and the like are likely to deteriorate as compared with the inside of the cell container, cell proliferation properties are improved by avoiding the excessive lengthening of retention time of the culture solution outside the cell container, whereby cell survival rate can be maintained. This makes it possible to cope with, for example, a small scale culture for an experiment and reduce the culture cost.

From the above viewpoints, the volume of a space defined by a diaphragm and a plane F including a surface of an outer edge part of the diaphragm on a side far from an apex of the diaphragm is preferably 2 cm$^3$ or more and 15 cm$^3$ or less, more preferably 2.5 cm$^3$ or more and 10 cm$^3$ or less, and still more preferably 3 cm$^3$ or more and 5 cm$^3$ or less.

For each point included in the arc-shaped portion of the diaphragm, the relative position in the diaphragm can be indicated by an angle. As illustrated in FIG. 3A, in a case where a perpendicular line Pr drawn from the apex (the center) of the diaphragm to the plane F is set as a reference line, the apex is at a position at an angle of 0° from the perpendicular line Pr. For an arbitrary point (for example, a point Pt in FIG. 3A) included in the arc-shaped portion (the portion except for the outer edge part) of the diaphragm, it is possible to define an angle (also referred to as an angle A) formed by a straight line drawn from a foot Ft of a perpendicular line Pr which is drawn from the apex (the center) of the diaphragm to the plane F to the arbitrary point and by the perpendicular line Pr. This angle A does not have a negative value regardless of the direction. Accordingly, the angle A becomes large as the distance from the center of the diaphragm increases, and the angle becomes 90° at the point that belongs to the plane F. The above-described arbitrary point included in the arc-shaped portion of the diaphragm is set on the lower surface (the surface on the side far from the apex) of the diaphragm in FIG. 3A.

The dome-shaped bulge shape of the movable part of the diaphragm is preferably a shape that is circularly symmetric to the perpendicular line Pr. The shape (excluding the connection point with the outer edge part) of the bulge-shaped cross section (the cross section including the perpendicular line Pr as illustrated in FIG. 3A) may be a hemisphere or an ellipse; however, it is not necessarily a regular shape such as a hemisphere or an ellipse. The shape thereof may be, for example, any shape in which a value obtained by carrying out a second order differentiation of coordinates in the vertical direction (the direction of the perpendicular line Pr) of the lower surface of the movable part of the diaphragm (the upper side in FIG. 3A is set as positive) by coordinates (the right side in FIG. 3A is set as positive) in the horizontal direction (the direction orthogonal to the perpendicular line Pr) in FIG. 3A is 0 or less except for the connection point to the outer edge part.

In the diaphragm of the diaphragm pump in the present disclosure, the thickness H of the diaphragm is in a range of 0.5 mm or more and 1.5 mm or less at any point in the region where the angle A is from 0° to 75°. In other words, the thickness H of the diaphragm is a variable that is determined at each point; however, both the minimum and the maximum values of this variable in the region where the angle A in the diaphragm is from 0° to 75° (the region X in FIG. 3A) are within a range of 0.5 mm or more and 1.5 mm or less. Here, the diaphragm pump has a form of an arc shape; however, the thickness H at each point means a dimension of the diaphragm in the direction perpendicular to the tangential line to the lower surface of the diaphragm at each point. Further, H refers to the thickness of the diaphragm at each point in the region where the angle A is from 0° to 75°, unless otherwise particularly specified.

In a case where the thickness of the diaphragm at each point in the region where the angle A is from 0° to 75° is 0.5 mm or more, the diaphragm damage during the culture can be effectively suppressed, and thus the culture can be continued easily. In addition, in a case where the thickness of the diaphragm at each point in the region where the angle A is from 0° to 75° is 1.5 mm or less, it is possible to avoid being difficult to reverse the diaphragm, and thus the function of the diaphragm pump can be sufficiently exhibited by reversing the diaphragm.

From the above viewpoints, the thickness at each point in the region where the angle A in the diaphragm is from 0° to 75° is preferably 0.6 mm or more and 1.4 mm or less, more preferably 0.7 mm or more and 1.3 mm or less, and still more preferably 0.8 mm or more and 1.2 mm or less.

The region where the angle A in the diaphragm is from 0° to 75° is a region of the apex the diaphragm and the periphery of the apex. In a case where the thickness in the region where the angle A is from 0° to 75° is uniform or the thickness at the apex of the diaphragm is slightly thicker than the peripheral region, the durability of the diaphragm is improved, and the diaphragm is hard to be torn. On the other hand, in a case where the thickness at the apex of the diaphragm is too large as compared with the thickness of the peripheral region, stress tends to be concentrated on the relatively thin portion, and thus the diaphragm is easily torn.

From these viewpoints, in the diaphragm in the present disclosure, in a case where a thickness of the diaphragm at the apex of the diaphragm is denoted by $H_T$, the thickness H of the diaphragm satisfies Expression 1 at any point in the region where the angle A is from 0° to 75°.

$$1 \leq H_T/H \leq 1.75 \qquad \text{(Expression 1)}$$

In a case where Expression 1 is satisfied, the effect of making the reversal movement of the diaphragm more supple can also be obtained in addition to the effect of suppressing diaphragm damage. The reversal movement of the diaphragm tends to be more supple as the thickness at the apex and the thickness at the periphery of the apex become uniformly closer to each other. In a case where the reversal movement of the diaphragm is supple, it is possible to avoid an increase in shear due to a rapid increase in flow rate in the cell suspension in the chamber 301, and thus the damage to cells is reduced.

As mentioned above, H is a variable representing the thickness of each point; however, from the above viewpoints, the value of $H_T/H$ is preferably 1 or more and 1.5 or less, more preferably 1 or more and 1.3 or less, and still more preferably 1 or more and 1.2 or less at any point in the region where the angle A in the diaphragm is from 0° to 75°.

In a case where a thickness of the diaphragm at the thickest point among points in a region (a region Y in FIG. 3A) where the angle A of the diaphragm is from 75° to 88° is $H_Y$ and a thickness of the diaphragm at a point (a point Z in FIG. 3A) where the angle A is 90° is denoted by $H_Z$, $H_Z$ and $H_Y$ preferably satisfy $H_Z < H_Y$, and the thickness H of the diaphragm preferably satisfies $H \leq H_Z$ at any point in the region where the angle A is from 0° to 75°. There are three main regions related to diaphragm tearing: a region where the angle A is from 0° to 75°, a region where the angle A is from 75° to 88°, and a point where the angle A is 90°. Basically, stress concentrates on the thinnest portion of the diaphragm, and tearing easily occurs at this point; however, in a case where only the thicknesses of all of the regions are increased, the impact at the time of diaphragm reversal will increase, and thus there is a risk that cell proliferation properties deteriorate. For this reason, it is preferable to make the maximum thickness of the region where the angle A is 75° to 88°, which is the region where stress is most easily concentrated in a case where the diaphragm is reversed, thicker than the thickness of the other regions, and in this sense, it is preferable to satisfy $H_Z < H_Y$. Further, in a case where the minimum value of the diaphragm thickness in the region where the angle A is from 75° to 88° is denoted by $H_S$, the thickness H of the diaphragm preferably satisfies $H \leq H_S$ at any point in the region where the angle A is from 0° to 75°.

$H_Y/H_Z$ is preferably more than 1 and 3 or less, more preferably more than 1 and 2 or less, still more preferably more than 1 and 1.5 or less, and even still more preferably more than 1 and 1.3 or less. The larger the thickness $H_Z$ at the point where the angle A is 90°, the greater the stress applied to the region where the angle A is from 75° to 88°. Therefore, it is preferable to make $H_Y$ larger (larger than $H_Z$). In addition, in a case where the upper limit value of the ratio of $H_Y$ to $H_Z$ is limited as described above, the reversal movement of the diaphragm can be made more supple, and the damage to cells due to the reversal movement of the diaphragm can be further reduced, whereby the proliferation properties of cells can be further improved, and the decrease in cell survival rate can be further suppressed. The point where the angle A is 90° is actually located on a circular line; however, in a case where there is a variation in the thickness of the diaphragm on this line, the maximum thickness on the above line is used as the thickness that is used for the comparison with $H_Y$.

The thickness H at any point in the region where the angle A in the diaphragm is from 0° to 75° preferably satisfies $H \leq H_Z$ and more preferably satisfies $H_Z < H_Y$ at the same time. The thicker the thickness of the diaphragm in the region where the angle A is from 0° to 75°, the larger the stress applied to the point where the angle A is 90° becomes large. Therefore, it is preferable to make the thickness $H_Z$ of the diaphragm at the point where the angle A is 90° larger (larger than the thickness at an arbitrary point in the region where the angle A is from 0° to 75°). The point where the angle A is 90° is actually located on a circular line; however, in a case where there is a variation in the thickness of the diaphragm on this line, the minimum thickness on the above line is used as the thickness that is used for the comparison with the thickness H at the arbitrary point in the region where the angle A is from 0° to 75°.

In addition, in a case where thickness H at any point in the region where the angle A in the diaphragm is from 0° to 75° satisfies $H \leq H_Z$ and satisfies $H_Z < H_Y$ at the same time, the thickness H at any point in the region where the angle A in the diaphragm is from 0° to 75° satisfies $H \leq H_Z$, which is preferable in suppressing the tearing of the diaphragm in the region where the angle A is from 75° to 88°.

Although the value of $H_Z$ is not particularly specified, it is preferably 0.5 mm or more and 2 mm or less, more preferably 0.7 mm or more and 1.9 mm or less, still more preferably 0.9 mm or more and 1.8 mm or less, and most preferably 1 mm or more and 1.7 mm or less.

Further, regarding the thickness H at any point in the region where the angle A in the diaphragm is from 0° to 75°, the value of $H_Z/H$ is preferably 1 or more and 3 or less, more preferably 1.1 or more and 2.5 or less, still more preferably 1.2 or more and 2.0 or less, and most preferably 1.3 or more and 1.8 or less. In a case where the upper limit value of the ratio of $H_Z$ to the thickness H at each point in the region where the angle A in the diaphragm is from 0° to 75° is limited as described above, since it is easy to avoid the excessive increase in the thickness of the diaphragm in the region the angle A is from 75° to 88°, the reversal movement of the diaphragm tends to be capable of being made more supple, the damage to cells due to the reversal movement of the diaphragm is further reduced, and cell proliferation properties is further improved, whereby cell survival rate tends to be capable of being further increased.

Further, the region where the angle A in the diaphragm is more than 88° and less than 90° is a region where the diaphragm is only slightly moved in a case where the diaphragm is reversed, as can be seen from FIG. 3A. The region where the angle A is more than 88° and less than 90° can be considered in the same manner as the point where the angle A is 90°, and thus the matters described for $H_Z$ may be applied in the same manner.

With respect to the thickness $H_Y$ of the diaphragm at the thickest point among points in the region where the angle A of the diaphragm is from 75° to 88°, the thickness H of the diaphragm preferably satisfies Expression 2 at any point in the region where the angle A is from 0° to 75°.

$$1 < H_Y/H \leq 3 \qquad \text{(Expression 2)}$$

As the thickness of the diaphragm in the region where the angle A is from 0° to 75° becomes thick, the stress applied to the region Y tends to become large. In a case where the thickness H at any point in the region where the angle A in the diaphragm is from 0° to 75° is set so that $H_Y/H$ exceeds 1, the region where the angle A is from 75° to 88° has a thickness sufficient to withstand the stress at the time of reversing the diaphragm, and thus the diaphragm is harder to be torn in the region where the angle A is from 75° to 88°. In a case where $H_Y/H$ is set to be 3 or less, the reversal movement of the diaphragm is maintained more supple, the damage to cells due to the reversal movement of the diaphragm is further reduced, and cell proliferation properties is further improved, whereby cell survival rate tends to be capable of being further increased.

From the above viewpoints, regarding the thickness H at any point in the region where the angle A in the diaphragm is from 0° to 75°, $H_Y/H$ is preferably more than 1 and 3 or less, more preferably 1.2 or more and 2.8 or less, still more preferably 1.4 or more and 2.6 or less, and even still more preferably 1.6 or more and 2.4 or less.

In addition, although the value of $H_Y$ is not particularly limited, it is preferably 1 mm or more and 3 mm or less, more preferably 1.2 mm or more and 2.8 mm or less, still more preferably 1.4 mm or more and 2.6 mm or less, and most preferably 1.6 mm or more and 2.4 mm or less.

Examples of a material of the diaphragm include a rubber material (for example, a chloroprene rubber, a nitrile rubber, an ethylene propylene diene rubber, a silicone rubber), an elastomer (for example, a thermoplastic polyester elastomer, a vinyl chloride resin-based thermoplastic elastomer), and fluororesin (for example, polytetrafluoroethylene).

The material of the diaphragm is not particularly limited as long as it can function as a diaphragm, and may be any elastic body. The material of the diaphragm is preferably a silicone rubber, more preferably a silicone rubber having a hardness of 45 or more and 54 or less, and still more preferably a silicone rubber having a hardness of 45 or more and 54 or less and having a tensile strength of 5 MPa or more and 8 MPa or less. Examples of the silicone rubber include TSE3457T manufactured by Momentive Performance Materials Japan LLC. The hardness of rubber can be measured by a durometer type A in accordance with JIS K6253: 2012. In addition, the tensile strength of rubber can be measured using a dumbbell specified in JIS in accordance with JIS K6249: 2003.

In a case where the hardness of the silicone rubber is 45 or more and 54 or less, the balance between the tearing resistance of the diaphragm and the suppleness of the reversal movement becomes better. In a case where the tensile strength of the silicone rubber is 5 MPa or more and 8 MPa or less, the balance between the tearing resistance of the diaphragm and the suppleness of the reversal movement becomes better. In a case where the hardness of the silicone rubber is 45 or more and 54 or less, and further, the tensile strength of the silicone rubber is 5 MPa or more and 8 MPa or less, the balance between the tearing resistance of the diaphragm and the suppleness of the reversal movement becomes further better. The suppleness of the reversal movement leads to the reduction of damage to cells, the improvement of cell proliferation properties, and the improvement of cell survival rate.

The tensile stress σ of the diaphragm at an elongation rate of 50% preferably satisfies Expression 3.

$$0.4\ \text{MPa} \le \sigma \le 1.5\ \text{MPa} \qquad \text{(Expression 3)}$$

The tensile stress σ of the diaphragm at an elongation rate of 50% can be obtained by the following method.

<Method for Measuring Tensile Stress of a Diaphragm at Elongation Rate of 50%>

A test piece having a size of a width of 10 mm and a length of 40 mm is cut out from a diaphragm, and a tensile test is performed on the test piece using a tensile tester STROGRAPH R2 (trade name) manufactured by Toyo Seiki Seisaku-sho, Ltd. Before the tensile test, the thickness of the test piece is measured using a high-accuracy Digimatic Micrometer MDH-25M (trade name) manufactured by Mitutoyo Corporation. In the tensile test, the distance between chucks is set to 10 mm, the tensile speed is set to 10 mm/min, and the tensile test is performed in the length direction of the test piece. The tensile stress at the time at which an elongation rate is 50% is calculated by dividing the load at the time at which the elongation rate is 50%, that is, in a case where the distance between the chucks is 15 mm, by the thickness of the test piece. Three test pieces are cut out from one diaphragm, the tensile test is repeated three times using the three test pieces, and the average value of the obtained values of the three tensile stress is used as the tensile stress of the diaphragm at an elongation rate of 50%.

In a case where the tensile stress σ at the time at which the elongation rate of the diaphragm is 50% is 0.4 MPa or more, it is possible to further avoid forceful reversing of the diaphragm at low pressure, and there is a tendency that damage to cells can be further reduced. In a case where the tensile stress σ at the time at which the elongation rate of the diaphragm is 50% is 1.5 MPa or less, the pressure required for reversing the diaphragm can be controlled in a more proper range, and the damage to cells due to the force of the reversal movement of the diaphragm tends to be capable of being reduced. Accordingly, in a case where the tensile stress σ at the time at which the elongation rate of the diaphragm is 50% is 0.4 MPa or more and 1.5 MPa or less, the reversal movement of the diaphragm can be made more supple, and the damage to cells is reduced, whereby the cell survival rate tends to be more easily maintained high.

From the above viewpoints, the tensile stress σ at the time at which the elongation rate of the diaphragm is 50% is preferably 0.4 MPa or more and 1.5 MPa or less, more preferably 0.5 MPa or more and 1.3 MPa or less, and 0, still more preferably 0.6 MPa or more and 1.1 MPa or less.

The method for culturing cells according to the present disclosure is a cell culture method that includes:

culturing cells in a cell suspension contained in a culture vessel; and extracting the cell suspension from the culture vessel with a diaphragm pump, in which a volume of a space defined by a diaphragm of the diaphragm pump and a plane F including a surface of an outer edge part of the diaphragm on a side far from an apex of the diaphragm is 1 cm$^3$ or more and 20 cm$^3$ or less, and in a case where an angle formed by a straight line connecting a foot of a perpendicular line which is drawn from the apex of the diaphragm to the plane F to each point in the diaphragm and by the perpendicular line is denoted by an angle A at each point, a thickness H of the diaphragm is within a range of 0.5 mm or more and 1.5 mm or less at any point in a region where the angle A is from 0° to 75°, and in a case where a thickness of the diaphragm at the apex of the diaphragm is denoted by $H_T$, the thickness H of the diaphragm satisfies Expression 1 at any point in the region where the angle A is from 0° to 75°.

$$1 \le H_T/H \le 1.75 \qquad \text{(Expression 1)}$$

Regarding the culture vessel and the diaphragm pump, the matters described in the description of the cell culture device according to the present disclosure are applied as they are.

Cells to be cultured in the method for culturing cells according to the present disclosure are not particularly limited, and examples thereof include animal cells, plant cells, eukaryotic cells such as yeast, and prokaryotic cells such as *Bacillus subtilis* and *Escherichia coli*. The cells may be ES cells, IPS cells, various stem cells, or the like.

The cells to be cultured in the method for culturing cells according to the present disclosure may be cells that produce a product. In a case where cells that produce a product are cultured, the product is produced by the cells, and in a case where the product is recovered, the substance production using the cells can be performed. The cells used cells for producing a product are not particularly limited and may be any one kind of animal cells, plant cells, eukaryotic cells such as yeast, or prokaryotic cells such as *Bacillus subtilis* and *Escherichia coli*. Animal cells such as CHO cells, BHK-21 cells, C127 cells, hybridoma cells, NS0 cells, and SP2/0-Ag14 cells are preferable, and CHO cells are more preferable in that many analyzes have been carried out and genetic engineering techniques have been established. Even in a case where the cells do not originally produce the desired product or the production amount is small, the desired product can be efficiently produced, for example, by introducing an expression vector, such as a plasmid, encoding a protein required for producing the product into the cell.

The product produced by the cells in the present disclosure is not particularly limited as long as it is a substance produced by the cells in a culture solution, and examples thereof include alcohols, enzymes, antibiotics, nucleic acids, recombinant proteins, and antibodies. Among them, the product is preferably a recombinant protein or an antibody and more preferably an antibody.

The concentration of cells in the cell suspension contained in the culture vessel is not particularly limited. However, since the higher cell concentration in the cell suspension contained inside the culture vessel allows the larger number of cells and the larger production amount of a product in a case where the cells produce the product, it is preferable that the cell concentration is high. The concentration of cells in the cell suspension contained in the culture vessel is increased after seeding and may be increased, for example, to a cell concentration in a range of $20\times10^6$ cells/mL or more and $150\times10^6$ cells/mL or less. Alternatively, the concentration of cells in the cell suspension contained in the culture vessel may be increased to a cell concentration in a range of $30\times10^6$ cells/mL or more and $120\times10^6$ cells/mL or less, may be increased to a cell concentration in a range of $40\times10^6$ cells/mL or more and $100\times10^6$ cells/mL or less, or may be increased to a cell concentration in a range of $50\times10^6$ cells/mL or more and $100\times10^6$ cells/mL or less. In the present disclosure, the "concentration" of cells refers to the number density, that is, the number of cells per unit volume.

As a medium used for cell culture, a liquid medium usually used for cell culture can be used. For example, OptiCHO (Life Technologies Corporation, 12681011) medium, Dulbecco's modified Eagle medium (DMEM), Eagle minimum essential medium (MEM), RPMI-1640 medium, RPMI-1641 medium, F-12K medium, Ham's F12 medium, Iscove's modified Dulbecco's medium (IMDM), McCoy's 5A medium, Leibovitz's L-15 medium, and EX-CELL (trade mark) 300 series (JRH Biosciences), CHO-S-SFMII (Invitrogen), CHO-SF (Sigma-Aldrich Co. LLC), CD-CHO (Invitrogen), ISCHO-V (FUJIFILM Irvine Scientific), PF-ACF-CHO (Sigma-Aldrich Co. LLC), and the like can be used.

Serum such as fetal calf serum (FCS) may be added to the medium. Alternatively, the medium may be a serum-free medium such as a fully synthetic medium.

The medium may be supplemented with additional components such as amino acids, salts, sugars, vitamins, hormones, growth factors, buffers, antibiotics, lipids, trace elements, and hydrolysates of plant proteins.

Although the pH of the medium varies depending on the cells to be cultured, the medium is generally pH 6.0 to 8.0, preferably pH 6.8 to 7.6, and more preferably pH 7.0 to 7.4.

The culture temperature is generally 30° C. to 40° C., preferably 32° C. to 37° C., and more preferably 36° C. to 37° C., and the culture temperature may be changed during the culture.

The culture may be performed in an atmosphere having a $CO_2$ concentration of 0% to 40% and preferably in an atmosphere having a $CO_2$ concentration of 2% to 10%.

In the culture, the medium can be replaced, aerated, and stirred as necessary.

The total cell suspension volume (including the cell suspension volume inside the culture vessel and the amount of the cell culture solution in elements such as the diaphragm pump and the flow path, where the elements are connected by a culture solution to the culture vessel) that is used in culture is not particularly limited as long as the total amount thereof can be used by the diaphragm pump in the disclosure; however, it is preferably 50 mL or more and 500 mL or less, more preferably 60 mL or more and 400 mL or less, still more preferably 70 mL or more and 300 mL or less, and most preferably 80 mL or more and 250 mL or less. As described above, in the present disclosure, the culture is carried out using a diaphragm pump having a diaphragm in which the volume of a space defined by the diaphragm and a plane F including a surface of an outer edge part of the diaphragm on a side far from an apex of the diaphragm is 1 $cm^3$ or more and 20 $cm^3$ or less. As described above, since the capacity of the diaphragm pump according to the present disclosure is limited, the culture is preferably a small-scale culture in which the cell suspension volume is small as in the case of the range described above. In a case where the volume of the culture solution is set to a value equal to or more than the above lower limit value, the culture is hard to be affected by disturbances such as liquid volume reduction and volatilization due to sampling, and thus the culture can be continued more easily, and in a case where the culture solution volume is set to a value equal to or less than the above upper limit value, the volume of the culture solution can be suppressed to a small scale, and thus the experimental cost tends to be suppressed.

The method for culturing cells according to the present disclosure may include stirring the cell suspension in the culture vessel with a stirring blade or may include gas-aerating the cell suspension with a sparger.

The cell culture is preferably a perfusion culture. The perfusion culture is a culture method in which fresh medium is added and at the same time used medium is removed. In a case of using the perfusion culture, it is also possible to achieve a high cell concentration exceeding $1\times10^8$ cells/mL. A typical perfusion culture begins with a batch culture start-up lasting 1 or 2 days, thereafter a fresh supplying culture medium is added to the culture continuously, stepwise, and/or intermittently, and the used medium is removed at the same time. In the perfusion culture, methods such as sedimentation, centrifugation, and filtration can be used to remove the used medium while maintaining the cell concentration. Perfusion may be continuous, stepwise, or intermittent, or a combination thereof.

The cell suspension is extracted from the culture vessel using a diaphragm pump. The cell suspension may be extracted from the culture vessel intermittently or continuously; however, it is preferable to continuously extract the cell suspension from the viewpoint of stably maintaining the state of the system. In a case where a reciprocating flow type diaphragm pump that does not use a check valve is used, the extraction of the cell suspension from the culture vessel and the returning of the extracted cell suspension to the culture vessel is carried out alternately where the diaphragm pump is operated. Such a case is also included in the range described by the above description of "the extraction of the cell suspension from the culture vessel". The extraction position of the cell suspension is not particularly limited as long as it is below the liquid surface, and can be, for example, near the bottom part of the culture vessel.

In a case where a diaphragm pump is used, a cross-flow type filter may be provided between the culture vessel and the diaphragm pump to perform filtration by the cross-flow type method. By such filtration, it is possible, for example, to recover a product produced by cells or remove waste products from the cell suspension.

However, in the method for culturing cells according to the present disclosure, the purpose of extracting the cell suspension from the culture vessel is not particularly limited, and the extracted cell suspension may be simply discarded to control the cell concentration or to remove waste products or may be subjected to a treatment of recovering cells by centrifugation or the like, or the recovery of a product produced by cells, removal of waste products, or the like may be carried out with a filter other than the cross-flow type filter. In these cases, the diaphragm pump may be a pump of a type that generates a reciprocating flow or a pump of a type that generates a unidirectional flow.

In the method for culturing cells according to the present disclosure, any matter described in the description of the cell culture device according to the present disclosure can be applied, and the method for culturing cells according to the present disclosure includes, for example, the following embodiments.

In the method for culturing cells according to the present disclosure, in a case where a thickness of the diaphragm at the thickest point among points in a region where the angle A of the diaphragm is from 75° to 88° is $H_Y$ and a thickness of the diaphragm at a point where the angle A is 90° is denoted by $H_Z$, $H_Z$ and $H_Y$ preferably satisfy $H_Z<H_Y$, and the thickness H of the diaphragm preferably satisfies $H \leq H_Z$ at any point in the region where the angle A is from 0° to 75°.

In the method for culturing cells according to the present disclosure, in a case where a thickness of the diaphragm at the thickest point among points in a region where the angle A of the diaphragm is from 75° to 88° is $H_Y$, the thickness H of the diaphragm preferably satisfies Expression 2 at any point in the region where the angle A is from 0° to 75°.

$$1 < H_Y/H \leq 3 \quad \text{(Expression 2)}$$

In the method for culturing cells according to the present disclosure, the material of the diaphragm is preferably a silicone rubber.

In the method for culturing cells according to the present disclosure, the tensile stress σ of the diaphragm at an elongation rate of 50% preferably satisfies Expression 3.

$$0.4 \text{ MPa} \leq \sigma \leq 1.5 \text{ MPa} \quad \text{(Expression 3)}$$

In the method for culturing cells according to the present disclosure, at the time at which the diaphragm pump is in operation, a pressure P in the inside of the diaphragm pump that drives the diaphragm preferably satisfies Expression 4.

$$\text{Atmospheric pressure} - 0.1 \text{ MPa} \leq P \leq \text{atmospheric pressure} + 0.1 \text{ MPa} \quad \text{(Expression 4).}$$

The pressure P in the inside of the diaphragm pump refers to a pressure in the space inside the diaphragm pump opposite to the cell suspension with the diaphragm being a boundary, in other words, refers to the pressure of the medium for driving the diaphragm pump. The pressure P in the inside of the diaphragm pump refers to the pressure inside the chamber 303 filled with a gas in FIG. 2. In other words, the above equation states that the absolute value of the difference between the atmospheric pressure and the pressure P is maintained at 0.1 MPa or less during the operation of the diaphragm pump, that is, the maximum value of the absolute value of the difference between the atmospheric pressure and the pressure P. It means that the value is 0.1 MPa or less. The pressure P in the inside of the diaphragm pump can be measured in a flow path or the like that is connected to the above-described space and can be measured, for example, in the flow path 59 in FIG. 2.

The pressure difference between the pressure P and the atmospheric pressure is the driving force for reversing the diaphragm. In a case where the absolute value of the pressure difference is set to 0.1 MPa or less, the reversal movement of the diaphragm can be carried out at a proper speed, the damage to cells can be further reduced, and tearing of the diaphragm tends to be further suppressed.

P is preferably [atmospheric pressure−0.1 MPa] or more and [atmospheric pressure+0.1 MPa] or less, more preferably [atmospheric pressure−0.08 MPa] or more and [atmospheric pressure+0.08 MPa] or less, still more preferably [atmospheric pressure−0.06 MPa] or more and [atmospheric pressure+0.06 MPa] or less, and even still more preferably [atmospheric pressure−0.05 MPa] or more and [atmospheric pressure+0.05 MPa] or less. However, in a case where the pressure difference between the pressure P and the atmospheric pressure is maintained at least at a certain level, the complete reversal of the diaphragm is prompted, which is preferable in terms of avoiding the retention of the cell suspension. For this reason, the maximum value (the maximum value in the diaphragm reversal cycle) of the absolute value of the pressure difference between the pressure P and the atmospheric pressure is preferably 1 kPa or more, more preferably 5 kPa or more, still more preferably 8 kPa or more, and even still more preferably 10 kPa (0.01 MPa) or more.

In the method for culturing cells according to the present disclosure, the cells contained in the cell suspension may be CHO cells.

The method for culturing cells according to the present disclosure may further include:
  subjecting the cell suspension extracted from the culture vessel to a separation treatment by which the extracted cell suspension is separated, by using a separation membrane, into a first solution having a cell concentration higher than a cell concentration in the cell suspension and a second solution having a cell concentration lower than the cell concentration in the cell suspension by a tangential flow filtration method,
  returning the first solution to the culture vessel; and
  adding a medium anew to the culture vessel.

The tangential flow filtration method is a method in which a liquid to be subjected membrane separation treatment is allowed to flow along a membrane surface of a separation membrane, whereby small-sized components are allowed to move on the permeation side of the separation membrane together with a liquid component, and large-sized components and the remaining liquid component are retained on the non-permeation side of the separation membrane. In the present disclosure, the non-permeation side of the separation membrane, that is, the supply side is also referred to as the primary side, and the permeation side of the separation membrane is also referred to as the secondary side.

In the membrane separation treatment by the tangential flow filtration method in the present disclosure, the cell suspension extracted from the culture vessel may be allowed to form a unidirectional flow that is parallel along the membrane surface of the separation membrane, or the direction of the flow of the cell suspension extracted from the culture vessel may be reversed at every predetermined time to form a reciprocating flow.

The cell suspension can be extracted from the culture vessel using a diaphragm pump. The cell suspension extracted from the culture vessel is sent to a filter unit for performing tangential flow filtration. The cell suspension may be extracted from the culture vessel to the filter unit intermittently or continuously; however, it is preferable to continuously extract the cell suspension from the viewpoint of stably maintaining the state of the system.

The filter unit includes, for example, a container and a separation membrane that partitions the space inside the container into a supply side and a permeation side and carries out a membrane separation treatment on the cell suspension extracted from the culture vessel. On the supply side of the separation membrane, the filter unit has an inlet port and an outlet port, each of which is connected to the flow path. In the membrane separation treatment by the tangential flow filtration method, in a case where the direction of the flow of the cell suspension extracted from the culture vessel is reversed at every predetermined time, the inlet port and the outlet port are replaced with each other by the reversal of the flow direction.

The separation membrane may be a mesh filter formed by weaving a fibrous member in a mesh shape or a hollow fiber membrane. As the hollow fiber membrane, a microfiltration membrane (an MF membrane) or an ultrafiltration membrane (a UF membrane) can be used.

The separation membrane does not allow live cells in the cell suspension to be permeated; however, it allows small molecules such as a target product in the cell suspension to be permeated. For example, in a case where an antibody is produced in animal cells, the size of the antibody is about 1 nm to 5 nm, whereas the order of magnitude of the size of the animal cell is 1 in terms of μm. For this reason, for example, in a case where a microfiltration membrane or an ultrafiltration membrane is used as the separation membrane, an antibody can be transferred to the secondary side through the separation membrane while keeping the live cells on the primary side. Further, since the size of the liquid component, for example, a water molecule is very small, a part of the liquid component also transfers to the secondary side together with the antibody. As a result, the cell concentration in the liquid remaining on the non-permeation side of the separation membrane increases. As described above, in a case where the separation by the tangential flow filtration method is carried out, the cell suspension sent to the filter unit remains on the primary side without permeating the separation membrane and is separated into a returning solution having a cell concentration higher than that of the cell suspension and a permeated solution having a cell concentration lower than that of the cell suspension, where the permeated solution has permeated the separation membrane and transferred to the secondary side. The permeated solution contains small molecules such as a product produced by cells. The cell concentration in the cell suspension referred to here means the live cell concentration in the cell suspension in the culture vessel. Further, in the present disclosure, the "cell concentration" refers to the "live cell concentration" unless otherwise particularly specified.

The returning solution remaining on the primary side flows out from the filter unit and returns to the inside of the culture vessel. For example, in a case where the direction of the flow in the space on the supply side of the filter unit in the tangential flow filtration is fixed unidirectionally, the cell suspension may be allowed to flow out from the outlet port by the liquid sending pressure due to a diaphragm pump having a check valve, thereby being returned to the culture vessel through a flow path connecting the outlet port to the culture vessel. In this case, the returning solution is returned to the culture vessel through a flow path different from the flow path through which the cell suspension in the culture vessel has passed at the time of moving to the inlet port of the filter unit, and thus a circulating flow is formed. On the other hand, in a case where the direction of the flow in the space on the supply side of the filter unit in the tangential flow filtration is reversed along with the passage of time by a diaphragm pump having no check valve, that is, in a case where the flow is reciprocated, the returning solution is returned to the culture vessel through the same flow path as the flow path through which the cell suspension in the culture vessel has passed at the time of moving to the inlet port of the filter unit, and in addition, the inlet port and the outlet port are reversed with each other as the direction of the flow is being reversed.

The permeated solution that has permeated the separation membrane contains small molecules such as a product produced by cells. The product in the permeated solution can be recovered and used for various purposes such as the production of pharmaceuticals and foods. The recovery of the product may be simply the recovery of the permeated solution, for example, the permeated solution in the tank. In a case of desiring to improve the purity of the product, change the solvent of the product, or change the form of the product to, for example, a power form, the permeated solution can be subjected to a further treatment.

Since the cell suspension sent from the culture vessel to the filter unit is separated into the permeated solution and the returning solution, the amount of the returning solution is smaller than the cell suspension volume sent to the filter unit. A fresh medium is supplied into the culture vessel to at least compensate for the difference between the cell suspension volume sent to the filter unit and the amount of the returning solution. In a case where the fresh medium is supplied into the culture vessel, it is possible to suppress an excessive increase in the cell concentration in the culture vessel, and it is possible to maintain the state of the cells in the culture vessel in a healthy state. That is, the benefits due to the perfusion culture can be obtained.

The fresh medium may be supplied into the culture vessel intermittently or continuously. Further, the cell suspension volume in the culture vessel is not necessary to be perfectly constant at all times and may be substantially constant in a range of a variation of, for example, ±10%, ±5%, and ±1%. The measurement of the cell suspension volume in the culture vessel is not necessary to be performed at all times and may be performed intermittently. Even in a case where there is a slight variation in the cell suspension volume, the benefits due to the perfusion culture can be obtained.

The method for producing a product according to the present disclosure is a method for producing a product, which includes:

culturing cells that produce a product by using the method for culturing cells according to the present disclosure; and recovering the product from the cell suspension of the cells.

In the method for producing a product according to the present disclosure, cells are cultured using the method for culturing cells according to the present disclosure, whereby the productivity of the product can be increased since the cell proliferation properties of the cells producing the product is good, and diaphragm damage can be suppressed.

As cells producing a product, the cells producing a product, which are exemplified above, can be used, and as a product, the products exemplified above can be produced. The product is preferably an antibody.

The product may be collectively recovered from the cell suspension at the end of the culture; however, it is preferable for the product to be recovered from the cell suspension at a predetermined frequency or continuously during the culture. In particular, the method for culturing cells, that is used in the method for producing a product, preferably further includes:

subjecting the cell suspension extracted from the culture vessel to a separation treatment by which the extracted cell suspension is separated, by using a separation membrane, into a first solution having a cell concentration higher than a cell concentration in the cell suspension and a second solution having a cell concentration lower than the cell concentration in the cell suspension by a tangential flow filtration method, returning the first solution to the culture vessel; and adding a medium anew to the culture vessel.

An embodiment in which the product is recovered from the second solution in the method for producing a product is preferable.

In general, the product has a drastically small size as compared with the cell. In a case where the cell suspension is extracted from the culture vessel, a product contained in the cell suspension is also extracted; however, in the separation treatment by the tangential flow filtration method, the product has a drastically small size as compared with the cell, and thus the product is contained as it is in the second solution without a significant decrease in concentration, whereas the cells remain mainly on the side of the first solution. As a result, the product can be recovered from the second liquid.

As described above, "recovering the product from the cell suspension of the cells" also includes the case of recovering the product from the treated product (for example, the second solution obtained by filtration) obtained by treating the cell suspension.

The recovery of the product may be simply the recovery of the cell suspension, the simple recovery of the second solution, or the like, where the cell suspension, the second solution, or the like may be collected in the tank or the like. In a case where the cell suspension has been recovered, the recovered cell suspension is preferably subjected to a treatment for separating the product from cells, and the cells can be removed from the solution by, for example, a filter or centrifugation. Further, even in a case where the second solution has been recovered, it may be subjected to a further treatment by a filter, centrifugation, or the like in order to further remove the cells. In addition, for the intended purpose of improving the purity of the product, changing the solvent of the product, or changing the form of the product to, for example, a power form, the solution can be subjected to a further treatment.

For example, the product contained in the solution can be purified by a purification treatment. The obtained product can be purified to high purity. In a case where the product is a polypeptide such as an antibody or a fragment thereof, the separation and purification of the product may be carried out by using the ordinary separation and purification method used for a polypeptide. For example, a chromatography column for affinity chromatography or the like, a filter, ultrafiltration, salting out, dialysis, SDS polyacrylamide gel electrophoresis, and isoelectric focusing electrophoresis can be appropriately selected and combined to separate and purify a polypeptide; however, the present invention is not limited to thereof The concentration of the obtained polypeptide can be measured by measuring the absorbance or by an enzyme-linked immunosorbent assay (ELISA).

An example of the cell culture device, the method for culturing cells, the method for producing a product, according to the present disclosure, will be collectively described with reference to FIG. 1. FIG. 1 is a view illustrating an example of a configuration of a cell culture device applicable to the method for culturing cells and the method for producing a product, according to the present disclosure.

A cell culture device 100 include a culture vessel 10 which contains cells together with a medium and in which the cells are cultured, a diaphragm pump 37 for extracting a cell suspension contained in the culture vessel 10 through a flow path 57, a pump P1 for supplying a fresh medium L2 contained in a medium supply container 20 into the culture vessel 10 through a flow path 56, a $CO_2$ supply container 31 for supplying a $CO_2$ gas into the culture vessel 10, an air supply container 32 for supplying air into the culture vessel 10, and an $O_2$ supply container 33 for supplying an $O_2$ gas into the culture vessel 10. A cell suspension L1 is contained in the culture vessel 10, and a stirring blade 11 for stirring the cell suspension L1 is provided therein. In a case where the stirring blade 11 is rotated, the cell suspension L1 contained in the inside of the culture vessel 10 is stirred, and thus the homogeneity of the cell suspension L1 is maintained. Further, a sampling port 35 is provided in the culture vessel.

The $CO_2$ gas in the $CO_2$ supply container 31 is sent to a flow meter 34 through a flow path 51, and further, supplied into the culture vessel 10 through a flow path 54. A regulator R1 and a pressure gauge M1 are provided in the flow path 51 to control the flow rate and monitor the pressure. A filter F1 is provided in the flow path 54 to purify the supplied gas. The air in the air supply container 32 is sent to a flow meter 34 through a flow path 52, and further, supplied into the culture vessel 10 through a flow path 54. A regulator R2 and a pressure gauge M2 are provided in the flow path 52 to control the flow rate and monitor the pressure. The $O_2$ gas in the $O_2$ supply container 33 is sent to a flow meter 34 through a flow path 53, and further, supplied into the culture vessel 10 through a flow path 55. A regulator R3 and a pressure gauge M3 are provided in the flow path 53 to control the flow rate and monitor the pressure. A filter F2 is provided in the flow path 55 to purify the supplied gas.

The cell suspension extracted through the flow path 57 is sent to a hollow fiber membrane filter 36, which is a tangential flow filtration type filter. The liquid that has permeated the hollow fiber membrane filter 36 is discharged from the hollow fiber membrane filter 36 by the pump P2 through a flow path 60. In a case where cells that are cultured are cells that produce a product, the product can be recovered by subjecting the liquid discharged from the hollow fiber membrane filter 36 to the flow path 60, to a purification treatment. The diaphragm pump 37 generates a reciprocating flow that is reciprocated in the flow path 57, the non-permeation side of the hollow fiber membrane filter 36, and the flow path 58. The chamber (the gas side chamber) of the diaphragm pump 37 opposite to the chamber (the liquid side chamber) on the side of the flow path 58 is filled with gas and is connected to the flow path 59. The air in the air supply container 38 flows into the gas side chamber of the diaphragm pump 37 through the flow path 59 by closing a solenoid valve V2 and opening a solenoid valve V1. As a result, the pressure in the gas side chamber becomes a pressure exceeding the atmospheric pressure, and the diaphragm of the diaphragm pump 37 has a substantially hemispherical shape, the apex of which is located in the liquid side chamber. On the contrary, in a case where the solenoid valve V2 is opened and the solenoid valve V1 is closed, a part of the air in the gas side chamber of the diaphragm pump 37 is discharged from the gas side chamber by a vacuum pump P3, the inside of the gas side chamber has a pressure lower than the atmospheric pressure, and thus the diaphragm of the diaphragm pump 37 is reversed to have a substantially hemispherical shape, the apex of which is located in the gas side chamber. A regulator R4 and a filter F3 are provided between the solenoid valve V1 and the diaphragm pump 37 to control the gas flow rate and purify the gas. Similarly, a regulator R5 is provided between the solenoid valve V2 and the filter F3 to control the gas flow rate. Since a pressure gauge M4 is provided in the flow path 59 and there is almost no pressure loss due to the filter F3, the pressure in the gas side chamber of the diaphragm pump 37 can be monitored by the pressure gauge M4. Arrows in FIG. 1 indicate moving directions of the liquid or the gas, or the movement of the diaphragm of the diaphragm pump 37. A flow path other than the flow path 59 through which the gas passes can be a pipe made of metal, plastic, or the like, and the flow path 59 through which the gas passes may be a pipe made of metal, plastic, or the like, and may be a tube formed of rubber or the like.

EXAMPLES

CHO cells were cultured using the cell culture device illustrated in FIG. 1.

First, 90 mL of a medium (trade name CD OptiCHO, manufactured by Thermo Fisher Scientific, Inc.) was added to a 250 mL culture vessel manufactured by ABLE INC., the temperature thereof was held at 37° C., and aeration was carried out from the upper surface of the culture vessel with air at 3.8 mL/min and with $CO_2$ at 0.2 mL/min, and the medium was left for 1 day. Next, CHO cells were seeded so that the cell concentration in the culture vessel was $2.0\times10^5$ cells/mL and the liquid volume in the culture vessel was 100 mL. Three days after seeding, a reciprocating flow of the cell suspension by the diaphragm pump under to be tested was generated so that the maximum pressure of the diaphragm gas side chamber (the maximum value of the absolute value of the difference from atmospheric pressure) became the predetermined pressure shown in Table 2, and this reciprocating flow was used to carry out filtration by the tangential flow filtration method. A hollow fiber membrane filter (T04-P20U-10-N) manufactured by Repligen Corporation was used for filtration. For replenishing the amount of the liquid lost from the culture system by filtration, the supply (the supplying of a fresh medium in the culture vessel) of a fresh medium (a mixture of a medium represented by a trade name of CD OptiCHO, manufactured by Thermo Fisher Scientific, Inc. and a medium represented by a trade name of Cell Boost 7a and 7b, manufactured by GE Healthcare) was carried out in parallel. The above filtration and supply of the fresh medium were carried out at a rate of 1.2 L/day. In the filtration by the tangential flow filtration method, the cell suspension was separated into a returning solution having a cell concentration higher than that of the cell suspension and a permeated solution having a cell concentration lower than that of the cell suspension, and the returning solution was returned to the inside of the culture vessel (the returning of the returning solution to the culture vessel). From the same day (3 days after seeding), oxygen was supplied into the culture vessel at a flow rate of 1 mL/min from the lower surface side of the culture vessel using a single tube having an inner diameter of 2 mm, one end of which was inserted into the culture vessel.

In the above culture, from the day when the cell concentration reached $80\times10^6$ cells/mL, an operation of extracting a predetermined cell suspension volume from the culture vessel (a cell bleeding operation) was carried out once a day so that the average cell concentration (the average value of the cell concentration at two time points by a twice-daily measurement of the cell concentration, described below) was about $80\times10^6$ cells/mL, and the culture was continued to the 28th day after seeding. In a case where the reciprocating flow of the cell suspension by the diaphragm pump stopped during the culture, the maximum value of the absolute value of the pressure in the diaphragm gas side chamber was increased to 0.1 MPa, and in a case where the reciprocating flow was still not restarted, the culture was stopped. After the culture was stopped, the presence or absence of tearing of the diaphragm was visually checked.

The cell suspension in the culture vessel was sampled once daily from the day of seeding to the day before the day on which the cell bleeding operation was started and twice daily before and after the cell bleeding operation after the day on which the cell bleeding operation was started, and the cell concentration and the cell viability were measured using the Vi-Cell XR (trade name) manufactured by BECKMAN COULTER Inc. The viability means the proportion of the number of live cells to the total number of dead cells and live cells.

In Comparative Example 1, XCell ATF2 manufactured by Repligen Corporation was used as the diaphragm pump to be tested. In Examples and Comparative Examples other than Comparative Example 1, a diaphragm pump including a diaphragm formed of the following materials in a metal container made of SUS316 was used. Diaphragms having sizes and characteristics shown in Table 1 and Table 2 were obtained by molding a silicone rubber (TSE3457T) manufactured by Momentive Performance Materials Japan LLC in Examples 1 to 11, 16, and 17, a silicone rubber (TSE3478T) manufactured by Momentive Performance Materials Japan LLC in Example 12, a silicone rubber (TSE221-5U) manufactured by Momentive Performance Materials Japan LLC in Example 13, a silicone rubber (TSE3466) manufactured by Momentive Performance Materials Japan LLC in Example 14, and a silicone rubber (KE-951-U) manufactured by Shin-Etsu Chemical Co., Ltd. in Example 15, each of the obtained diaphragms was contained in the above metal container, and a device capable of switching, at every predetermined time, the pressure (the pressure in the gas side chamber) in the pump to a positive pressure or a negative pressure by air and by a vacuum pump and a solenoid valve was used.

The thickness of the diaphragm at each position of the diaphragm was measured using a thickness gauge (trade name: thickness gauge 547-31, manufactured by Mitutoyo Corporation) before using the diaphragm pump for the above culture. The tensile stress at the time at which the elongation rate of the diaphragm was 50% was measured according to the following procedure. A test piece E1 having a width of 10 mm and a length of 40 mm was cut out from a diaphragm, and a tensile test was performed on the test piece E1 using a tensile tester STROGRAPH R2 (trade name) manufactured by Toyo Seiki Seisaku-sho, Ltd. Before the tensile test, the thickness of the test piece E1 was measured using a high-accuracy Digimatic Micrometer MDH-25M (trade name) manufactured by Mitutoyo Corporation. In the tensile test, the distance between chucks was set to 10 mm, the tensile speed was set to 10 mm/min, and the tensile test was performed in the length direction of the test piece E1. The tensile stress at the time at which an elongation rate is 50% is calculated by dividing the load at the time at which the elongation rate is 50%, that is, in a case where the distance between the chucks is 15 mm, by the thickness of the test piece E1. Three test pieces were cut out from one diaphragm, the tensile test was repeated three times using the three test pieces E1, and the average value of the obtained values of the three tensile stress was used as the tensile stress of the diaphragm at an elongation rate of 50%.

Based on the presence or absence of tearing of the diaphragm, the cell concentration, and the viability, which were observed above, the evaluation was carried out according to the following evaluation standards.

<State of Diaphragm>
  A: The diaphragm was not torn, cracked, and discolored after use.
  B: The diaphragm was partially discolored white after use.
  C: The diaphragm was partially cracked after use.
  D: The diaphragm was torn during the culture.

<Cell Proliferation Properties>
  A: Within 10 days after seeding, the cell concentration increased to $80 \times 10^6$ cells/mL or more.
  B: Within 10 days after seeding, the cell concentration did not reach $80 \times 10^6$ cells/mL.

<Average Viability>
  A: The average value of viability during the 28-day culture period was 95% or more.
  B: The average value of viability during the 28-day culture period was 90% or more and less than 95%.
  C: The average value of viability during the 28-day culture period was 85% or more and less than 90%.

Figure 4B:
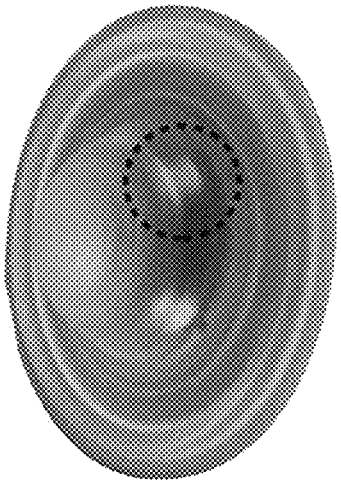
In FIGS. 4A to 4D are views illustrating evaluation standards for a state of a diaphragm in Examples and Comparative Examples.
Figure 4D:
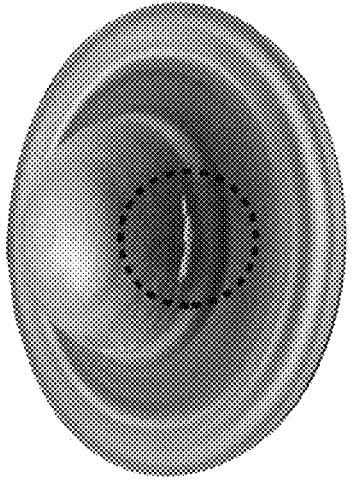
Figure 4A:
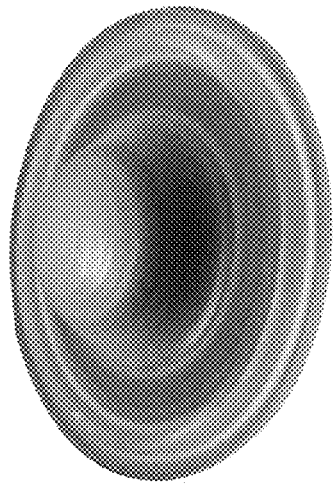
Figure 4C:
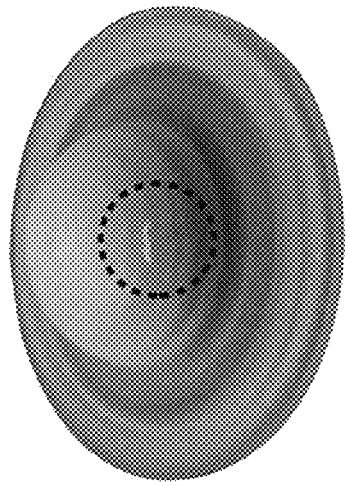
Figure 5:
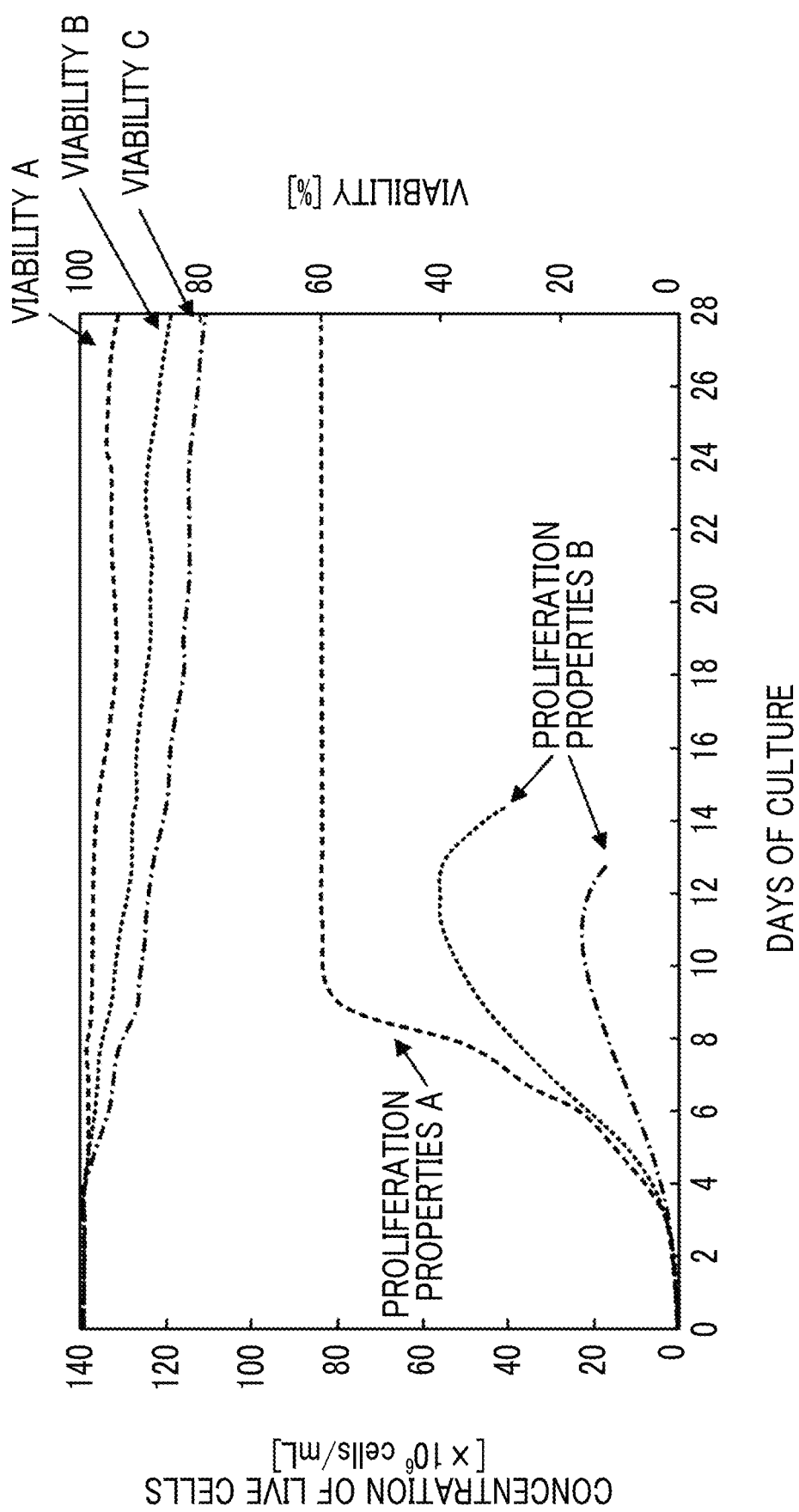
FIG. 5 is a graph showing evaluation standards for proliferation properties and viability in Examples and Comparative Examples.

Regarding the evaluation of the state of the diaphragm, a specific example of the specific state is illustrated in FIGS. 4A to 4D. In FIG. 4A, a state of the diaphragm in the state A in the above-described evaluation standards is illustrated, in FIG. 4B, a state of the diaphragm in the state B in the above-described evaluation standards is illustrated, in FIG. 4C, a state of the diaphragm in the state C in the above-described evaluation standards is illustrated, and in FIG. 4D, a state of the diaphragm in the state D in the above-described evaluation standards is illustrated. In FIGS. 4A to 4D, clear abnormalities are observed in the state B, the state C, and the state D; however, the diaphragm is operable in the states B and the state C. For this reason, it can be said that the state A to the state C are within the permissible range. However, in a case where the diaphragm is torn during the culture as in the state D, the function (the generation of a reciprocating flow) as a diaphragm pump cannot be fulfilled, and thus the culture cannot be continued. Further, a specific example of the evaluation of cell proliferation properties and average viability is illustrated in FIG. 5. The change curve shown as proliferation properties in FIG. 5 represents the relationship between the days of culture and the cell concentration (the live cell concentration) after seeding. In a case where cell proliferation proceeds smoothly as in the case of the proliferation properties A in FIG. 5, a high cell concentration can be obtained, and the high cell concentration can be maintained. On the other hand, in a case where the evaluation of cell proliferation properties is B, the cell concentration typically reaches a maximum at a relatively low cell concentration and then decreases, as illustrated in FIG. 5. The change curve shown as the viability in FIG. 5 represents the relationship between the days of culture after seeding and the viability (the cell survival rate=the number of live cells/(the number of live cells+the number of dead cells)). The viability after seeding tends to decrease gradually, and the decreasing tendency becomes more remarkable as the rank of the average viability evaluation goes down. However, regarding the average viability, even the rank A is within the permissible range. Regarding the permissible range in the evaluation for cells, there is the premise that the cell proliferation properties are within the permissible range (the proliferation properties A), and thus the higher viability indicates the more preferred range.

The configuration of each of the examples is shown in Table 1 and Table 2 below together with the evaluation results.

TABLE 1

| Examples | Volume of diaphragm (cm³) | Maximum thickness of region where angle A is 0° to 75° Xmax (nm) | Minimum thickness of region where angle A is 0° to 75° Xmin (nm) | Maximum value of ratio of thickness at apex to thickness of region where angle A is 0° to 75° $(H_T/H)$max | Minimum value of ratio of thickness at apex to thickness of region where angle A is 0° to 75° $(H_T/H)$min | Thickness $H_Z$ at point where angle A is 90° (mm) | Maximum thickness $H_Y$ at point where angle A is 75° to 88° (mm) |
|---|---|---|---|---|---|---|---|
| Example 1 | 3.9 | 1.0 | 1.0 | 1.0 | 1.0 | 1.6 | 1.7 |
| Example 2 | 6.4 | 1.0 | 1.0 | 1.0 | 1.0 | 1.6 | 1.7 |
| Example 3 | 3.0 | 1.0 | 1.0 | 1.0 | 1.0 | 1.6 | 1.7 |
| Example 4 | 3.9 | 1.3 | 1.3 | 1.0 | 1.0 | 1.6 | 1.7 |
| Example 5 | 3.9 | 0.7 | 0.7 | 1.0 | 1.0 | 1.6 | 1.7 |
| Example 6 | 3.9 | 1.2 | 0.8 | 1.5 | 1.0 | 1.6 | 1.7 |
| Example 7 | 3.9 | 1.3 | 1.3 | 1.0 | 1.0 | 1.6 | 1.4 |
| Example 8 | 3.9 | 1.3 | 1.3 | 1.0 | 1.0 | 1.2 | 1.7 |
| Example 9 | 3.9 | 1.3 | 1.3 | 1.0 | 1.0 | 1.2 | 1.2 |
| Example 10 | 3.9 | 1.0 | 1.0 | 1.0 | 1.0 | 1.6 | 2.5 |
| Example 11 | 3.9 | 1.0 | 1.0 | 1.0 | 1.0 | 1.6 | 3.3 |
| Example 12 | 3.9 | 1.0 | 1.0 | 1.0 | 1.0 | 1.6 | 1.7 |
| Example 13 | 3.9 | 1.0 | 1.0 | 1.0 | 1.0 | 1.6 | 1.7 |
| Example 14 | 3.9 | 1.0 | 1.0 | 1.0 | 1.0 | 1.6 | 1.7 |
| Example 15 | 3.9 | 1.0 | 1.0 | 1.0 | 1.0 | 1.6 | 1.7 |
| Example 16 | 3.9 | 1.0 | 1.0 | 1.0 | 1.0 | 1.6 | 1.7 |
| Example 17 | 3.9 | 1.0 | 1.0 | 1.0 | 1.0 | 1.6 | 1.7 |
| Comparative example 1 | 35 | 2.2 | 1.2 | 1.8 | 1.0 | 1.6 | 1.7 |
| Comparative example 2 | 3.9 | 0.4 | 0.4 | 1.0 | 1.0 | 1.6 | 1.7 |
| Comparative example 3 | 3.9 | 1.7 | 1.7 | 1.0 | 1.0 | 1.6 | 1.7 |
| Comparative example 4 | 3.9 | 2.2 | 1.2 | 1.8 | 1.0 | 1.6 | 1.7 |

TABLE 1-continued

| Examples | Volume of diaphragm (cm³) | Maximum thickness of region where angle A is 0° to 75° Xmax (nm) | Minimum thickness of region where angle A is 0° to 75° Xmin (nm) | Maximum value of ratio of thickness at apex to thickness of region where angle A is 0° to 75° ($H_T/H$)max | Minimum value of ratio of thickness at apex to thickness of region where angle A is 0° to 75° ($H_T/H$)min | Thickness $H_Z$ at point where angle A is 90° (mm) | Maximum thickness $H_Y$ at point where angle A is 75° to 88° (mm) |
|---|---|---|---|---|---|---|---|
| Comparative example 5 | 3.9 | 1.1 | 0.6 | 1.8 | 1.0 | 1.6 | 1.7 |
| Comparative example 6 | 3.9 | 1.2 | 0.8 | 1.0 | 0.7 | 1.6 | 1.7 |

TABLE 2

| Examples | $H_Z < H_Y$ | $H_Z \geq H_Y$ at all times | Maximum value of ratio $H_Y/X$ ($H_Y/X$)max | Minimum value of ratio $H_Y/X$ ($H_Y/X$)min | Tensile stress σ at elongation rate of 50% (MPa) | Maximum value of absolute value of pressure to diaphragm (MPa) | State of diaphragm | Cell proliferation properties | Average viability |
|---|---|---|---|---|---|---|---|---|---|
| Example 1 | Satisfied | Satisfied | 1.7 | 1.7 | 0.8 | 0.05 | A | A | A |
| Example 2 | Satisfied | Satisfied | 1.7 | 1.7 | 0.8 | 0.05 | A | A | B |
| Example 3 | Satisfied | Satisfied | 1.7 | 1.7 | 0.8 | 0.05 | A | A | B |
| Example 4 | Satisfied | Satisfied | 1.3 | 1.3 | 0.8 | 0.05 | A | A | C |
| Example 5 | Satisfied | Satisfied | 2.4 | 2.4 | 0.8 | 0.05 | B | A | B |
| Example 6 | Satisfied | Satisfied | 2.1 | 1.4 | 0.8 | 0.05 | A | A | C |
| Example 7 | Not satisfied | Satisfied | 1.1 | 1.1 | 0.8 | 0.05 | B | A | C |
| Example 8 | Satisfied | Not satisfied | 1.3 | 1.3 | 0.8 | 0.05 | B | A | C |
| Example 9 | Not satisfied | Not satisfied | 0.9 | 0.9 | 0.8 | 0.05 | C | A | C |
| Example 10 | Satisfied | Satisfied | 2.5 | 2.5 | 0.8 | 0.05 | A | A | B |
| Example 11 | Satisfied | Satisfied | 3.3 | 3.3 | 0.8 | 0.05 | A | A | C |
| Example 12 | Satisfied | Satisfied | 1.7 | 1.7 | 0.6 | 0.05 | A | A | B |
| Example 13 | Satisfied | Satisfied | 1.7 | 1.7 | 0.3 | 0.05 | A | A | C |
| Example 14 | Satisfied | Satisfied | 1.7 | 1.7 | 1.2 | 0.05 | A | A | B |
| Example 15 | Satisfied | Satisfied | 1.7 | 1.7 | 1.6 | 0.05 | A | A | C |
| Example 16 | Satisfied | Satisfied | 1.7 | 1.7 | 0.8 | 0.07 | A | A | B |
| Example 17 | Satisfied | Satisfied | 1.7 | 1.7 | 0.8 | 0.12 | A | A | C |
| Comparative Example 1 | Satisfied | Not satisfied | 1.4 | 0.8 | 0.8 | 0.05 | — | B | — |
| Comparative Example 2 | Satisfied | Satisfied | 4.3 | 4.3 | 0.8 | 0.05 | D | — | — |
| Comparative Example 3 | Satisfied | Not satisfied | 1.0 | 1.0 | 0.8 | 0.05 | — | B | — |
| Comparative Example 4 | Satisfied | Not satisfied | 1.4 | 0.8 | 0.8 | 0.05 | D | A | — |
| Comparative Example 5 | Satisfied | Satisfied | 2.8 | 1.5 | 0.8 | 0.05 | D | A | — |
| Comparative Example 6 | Satisfied | Satisfied | 2.1 | 1.4 | 0.8 | 0.05 | D | A | — |

Figure 6:
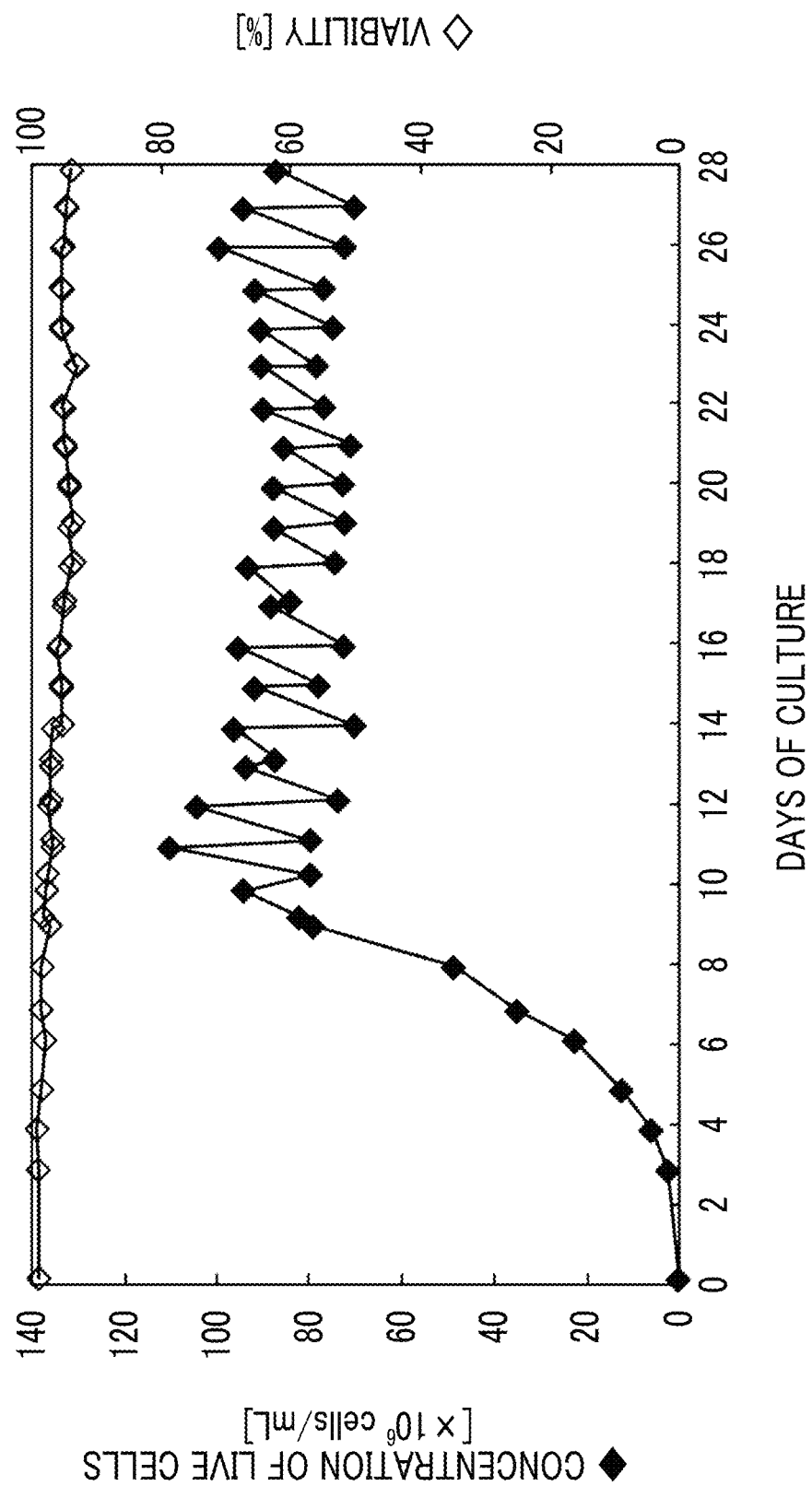
FIG. 6 is a graph showing changes in cell concentration and viability in Example 1.

In Example 1 to Example 17 of the present application, in which the volume of a space defined by a diaphragm and a plane including a surface of the outer edge part of the diaphragm on a side far from an apex of the diaphragm is 1 cm³ or more and 20 cm³ or less, the thickness H of the diaphragm is in a range of 0.5 mm or more and 1.5 mm or less at any point in the region where the angle A is from 0° to 75°, and the thickness H of the diaphragm satisfies Expression 1 below at any point in the region where the angle A is from 0° to 75°, $$1 \leq H_T/H \leq 1.75 \quad \text{(Expression 1)}$$

the diaphragm damage was suppressed, good cell proliferation properties were obtained, and a good cell survival rate was obtained. For example, in Example 1, in addition to the fact that no abnormality was observed in the diaphragm after the culture, the good cell proliferation properties and the good viability shown in FIG. 6 were exhibited. In FIG. 6, the white-empty diamonds indicate the change in viability, and the black-filled diamonds indicate the change in cell concentration (live cell concentration). In FIG. 6, the oscillating variation in the cell concentration is observed after the 10th day since the cell concentration is decreased due to the cell bleeding operation and then increased again due to the subsequent proliferation.

On the other hand, in Comparative Example 1 in which the volume of the space was more than 20 cm³, the maximum value of the diaphragm thickness H in the region where the angle A is from 0° to 75° was more than 1.5 mm, and the maximum value of $H_T/H$ was more than 1.75, the increase in cell concentration stopped at a low cell concentration, and sufficient cell proliferation properties could not be obtained. In this case, the culture was stopped since the cell concentration began to decrease. As a result, the diaphragm state after the culture of 28 days and the average viability for 28 days could not be measured. These results indicate that even in a case where a conventional diaphragm pump for culture is used, cell proliferation properties cannot be maintained in the small-scale culture.

Further, in Comparative Example 2 in which the minimum value of the diaphragm thickness H in the region where the angle A was from 0° to 75° was less than 0.5 mm, the diaphragm was torn during the culture before the 10th day after seeding and before the cell concentration reached $80 \times 10^6$ cells/mL. As a result, the cell proliferation properties and the average viability for 28 days could not be measured.

In Comparative Example 3 in which the maximum value of the diaphragm thickness H in the region where the angle A was from 0° to 75° was more than 1.5 mm, the increase in cell concentration stopped at a low cell concentration, and sufficient cell proliferation properties could not be obtained. In this case, the culture was stopped since the cell concentration began to decrease. As a result, the diaphragm state after the culture of 28 days and the average viability during 28 days could not be measured.

In Comparative Example 4 in which the maximum value of the diaphragm thickness H in the region where the angle A was from 0° to 75° was more than 1.5 mm and the maximum value of $H_T/H$ was more than 1.75, the diaphragm was torn during the culture. As a result, the average viability for 28 days could not be measured.

In Comparative Example 5 in which the maximum value of $H_T/H$ was more than 1.75, the diaphragm was torn during the culture. As a result, the average viability for 28 days could not be measured. It is noted that the diaphragm in Comparative Example 5 corresponds to a diaphragm which is reduced in a similar shape with respect to XCell ATF2 manufactured by Repligen Corporation Comparative Example 1. As described above, it has been shown that even in a case where the conventional diaphragm pump for culture is made smaller as it is, it is not possible to achieve both the suppression of diaphragm damage and the high cell proliferation properties.

In Comparative Example 6 in which the minimum value of $H_T/H$ was less than 1, the diaphragm was torn during the culture. As a result, the average viability for 28 days could not be measured.

From the above results, it can be seen that in a case where only a diaphragm pump in which the volume of a space defined by a diaphragm and a plane including a surface of the outer edge part of the diaphragm on a side far from an apex of the diaphragm is 1 cm³ or more and 20 cm³ or less, the thickness H of the diaphragm is in a range of 0.5 mm or more and 1.5 mm or less at any point in the region where the angle A is from 0° to 75°, and the thickness H of the diaphragm satisfies Expression 1 at any point in the region where the angle A is from 0° to 75° used, it is possible to achieve both the high cell proliferation properties and the suppression of diaphragm tearing in the small-scale culture.

Further, from the comparison of the results of Example 4 with the results of Examples 7 to Example 9, it can be seen that the diaphragm damage tends to be further suppressed in a case where $H_Z<H_Y$ and $H_Z \geq H$ are satisfied. In addition, from the comparison of the results of Example 10 with the results of Example 11, it can be seen that in a case where the value of $H_Y/H$ is set to a value in a range of more than 1 and 3 or less, a higher cell survival rate tends to be obtained. From the comparison of the results of Example 12 and Example 14 with the results of Example 13 and Example 15, it can be seen that in a case where the tensile stress σ at an elongation rate of the diaphragm of 50% is set to a value within a range of 0.4 MPa or more and 1.5 MPa or less, a higher cell survival rate tends to be obtained. From the comparison of the results of Example 1 and Example 16 with the results of Example 17, it can be seen that the absolute value of the pressure difference between the pressure P in the inside of the diaphragm pump and the atmospheric pressure is controlled to be 0.1 MPa or less, a higher cell survival rate tends to be obtained.

As described above, according to the present disclosure, it is possible to provide a cell culture device, a method for culturing cells, and a method for producing a product, with which both good cell proliferation properties and the suppression of diaphragm damage can be achieved in a case where a cell suspension is extracted with a diaphragm pump having a small capacity.

All documents, patent applications, and technical standards described in the present specification are incorporated in the present specification by reference, to the same extent as in the case where each of the documents, patent applications, and technical standards is specifically and individually described.

The means for solving the problems further includes the following aspects.

<2> The cell culture device according to <1>, in which in a case where a thickness of the diaphragm at a thickest point among points in a region where the angle A of the diaphragm is from 75° to 88° is $H_Y$ and a thickness of the diaphragm at a point where the angle A is 90° is denoted by $H_Z$, $H_Z$ and $H_Y$ satisfy $H_Z<H_Y$, and the thickness H of the diaphragm satisfies $H \leq H_Z$ at any point in the region where the angle A is from 0° to 75°.

<3> The cell culture device according to <1> or <2>, in which in a case where a thickness of the diaphragm at a thickest point among points in a region where the angle A of the diaphragm is from 75° to 88° is denoted by $H_Y$, the thickness H of the diaphragm satisfies Expression 2 at any point in the region where the angle A is from 0° to 75°, $$1 < H_Y/H \leq 3 \quad \text{(Expression 2)}.$$

<4> The cell culture device according to any one of <1> to <3>, in which a material of the diaphragm is silicone rubber.

<5> The cell culture device according to any one of <1> to <4>, in which a tensile stress σ of the diaphragm at an elongation rate of 50% satisfies Expression 3, $$0.4 \text{ MPa} \leq \sigma \leq 1.5 \text{ MPa} \quad \text{(Expression 3)}.$$

<7> The method for culturing cells according to <6>, in which in a case where a thickness of the diaphragm at a thickest point among points in a region where the angle A of the diaphragm is from 75° to 88° is $H_Y$ and a thickness of the diaphragm at a point where the angle A is 90° is denoted by $H_Z$, $H_Z$ and $H_Y$ satisfy $H_Z<H_Y$, and the thickness H of the diaphragm satisfies $H \leq H_Z$ at any point in the region where the angle A is from 0° to 75°.

<8> The method for culturing cells according to <6> or <7>, in which in a case where a thickness of the diaphragm at a thickest point among points in a region where the angle A of the diaphragm is from 75° to 88° is denoted by $H_Y$, the thickness H of the diaphragm satisfies Expression 2 at any point in the region where the angle A is from 0° to 750, $$1 < H_Y/H \leq 3 \quad \text{(Expression 2)}.$$

<9> The method for culturing cells according to any one of <6> to <8>, in which a material of the diaphragm is silicone rubber.

<10> The method for culturing cells according to any one of <6> to <9>, in which a tensile stress σ of the diaphragm at an elongation rate of 50% satisfies Expression 3, $$0.4 \text{ MPa} \leq \sigma \leq 1.5 \text{ MPa} \quad \text{(Expression 3)}.$$

<11> The method for culturing cells according to any one of <6> to <10>,
in which at a time at which the diaphragm pump is in operation, a pressure P in an inside of the diaphragm pump that drives the diaphragm satisfies Expression 4, $$\text{atmospheric pressure} - 0.1 \text{ MPa} \leq P \leq \text{atmospheric pressure} + 0.1 \text{ MPa} \quad \text{(Expression 4)}.$$

<12> The method for culturing cells according to any one of <6> to <11>, in which the cells are CHO cells.

<13> The method for culturing cells according to any one of <6> to <12>, further comprising:
subjecting the cell suspension extracted from the culture vessel to a separation treatment by which the extracted cell suspension is separated, by using a separation membrane, into a first solution having a cell concentration higher than a cell concentration in the cell suspension and a second solution having a cell concentration lower than the cell concentration in the cell suspension by a tangential flow filtration method,
returning the first solution to the culture vessel; and
adding a medium anew to the culture vessel.

<14> A method for producing a product, comprising:
culturing cells that produce a product, using the method for culturing cells according to any one of <6> to <13>; and
recovering the product from a cell suspension of the cells.

<15> The method for producing a product according to <14>, in which the product is an antibody.

According to the embodiments of the present invention, there are provided a cell culture device and a method for culturing cells, with which both good cell proliferation properties and the suppression of diaphragm damage can be achieved in a case where a cell suspension is extracted with a diaphragm pump having a small capacity, and a method for producing a product using the method for culturing cells.

What is claimed is:

1. A cell culture device comprising:
a culture vessel containing a cell suspension; and
a diaphragm pump for extracting the cell suspension from the culture vessel,
wherein a volume of a space defined by a diaphragm of the diaphragm pump and a plane F including a surface of an outer edge part of the diaphragm on a side far from an apex of the diaphragm is 1 cm³ or more and 20 cm³ or less,
in a case where an angle formed by a straight line connecting a foot of a perpendicular line which is drawn from the apex of the diaphragm to the plane F to each point in the diaphragm and by the perpendicular line is denoted by an angle A at each point, a thickness H of the diaphragm is within a range of 0.5 mm or more and 1.5 mm or less at any point in a region where the angle A is from 0° to 75°,
in a case where a thickness of the diaphragm at the apex of the diaphragm is denoted by $H_T$, the thickness H of the diaphragm satisfies Expression 1 at any point in the region where the angle A is from 0° to 75°, $$1 \leq H_T/H \leq 1.75 \quad \text{(Expression 1), and}$$

wherein in a case where a thickness of the diaphragm at a thickest point among points in a region where the angle A of the diaphragm is from 75° to 88° is $H_Y$ and a thickness of the diaphragm at a point where the angle A is 90° is $H_Z$, $H_Z$ and $H_Y$ satisfy $H_Z<H_Y$, and
the thickness H of the diaphragm satisfies $H \leq H_Z$ at any point in the region where the angle A is from 0° to 75°.

2. The cell culture device according to claim 1,
wherein in a case where a thickness of the diaphragm at a thickest point among points in a region where the angle A of the diaphragm is from 75° to 88° is denoted by $H_Y$, the thickness H of the diaphragm satisfies Expression 2 at any point in the region where the angle A is from 0° to 75°, $$1 < H_Y/H \leq 3 \quad \text{(Expression 2)}.$$

3. The cell culture device according to claim 1,
wherein in a case where a thickness of the diaphragm at a thickest point among points in a region where the angle A of the diaphragm is from 75° to 88° is denoted by $H_Y$, the thickness H of the diaphragm satisfies Expression 2 at any point in the region where the angle A is from 0° to 75°, $$1 < H_Y/H \leq 3 \quad \text{(Expression 2)}.$$

4. The cell culture device according to claim 1,
wherein a material of the diaphragm is silicone rubber.

5. The cell culture device according to claim 1,
wherein a tensile stress σ of the diaphragm at an elongation rate of 50% satisfies Expression 3, $$0.4 \text{ MPa} \leq \sigma < 1.5 \text{ MPa} \quad \text{(Expression 3)}.$$

6. A method for culturing cells, comprising:
culturing cells in a cell suspension contained in a culture vessel; and
extracting the cell suspension from the culture vessel with a diaphragm pump,
wherein a volume of a space defined by a diaphragm of the diaphragm pump and a plane F including a surface of an outer edge part of the diaphragm on a side far from an apex of the diaphragm is 1 cm³ or more and 20 cm³ or less,
in a case where an angle formed by a straight line connecting a foot of a perpendicular line which is drawn from the apex of the diaphragm to the plane F to each point in the diaphragm and by the perpendicular line is denoted by an angle A at each point, a thickness H of the diaphragm is within a range of 0.5 mm or more and 1.5 mm or less at any point in a region where the angle A is from 0° to 75°,
in a case where a thickness of the diaphragm at the apex of the diaphragm is denoted by $H_T$, the thickness H of the diaphragm satisfies Expression 1 at any point in the region where the angle A is from 0° to 75°, $$1 \leq H_T/H \leq 1.75 \quad \text{(Expression 1), and}$$

wherein in a case where a thickness of the diaphragm at a thickest point among points in a region where the angle A of the diaphragm is from 75° to 88° is denoted by $H_Y$ and a thickness of the diaphragm at a point where the angle A is 90° is denoted by $H_Z$, $H_Z$ and $H_Y$ satisfy $H_Z<H_Y$, and
the thickness H of the diaphragm satisfies $H \leq H_Z$ at any point in the region where the angle A is from 0° to 75°.

7. The method for culturing cells according to claim 6,
wherein in a case where a thickness of the diaphragm at a thickest point among points in a region where the angle A of the diaphragm is from 75° to 88° is denoted by $H_Y$, the thickness H of the diaphragm satisfies Expression 2 at any point in the region where the angle A is from 0° to 75°, $1 < H_Y/H \leq 3$ (Expression 2).

8. The method for culturing cells according to claim 6, wherein a material of the diaphragm is silicone rubber.

9. The method for culturing cells according to claim 6, wherein a tensile stress σ of the diaphragm at an elongation rate of 50% satisfies Expression 3, $0.4\ \text{MPa} \leq \sigma \leq 1.5\ \text{MPa}$ (Expression 3).

10. The method for culturing cells according to claim 6, wherein at a time at which the diaphragm pump is in operation, a pressure P in an inside of the diaphragm pump that drives the diaphragm satisfies Expression 4, atmospheric pressure−0.1 MPa ≤ $P$ ≤ atmospheric pressure+0.1 MPa (Expression 4).

11. The method for culturing cells according to claim 6, wherein the cells are CHO cells.

12. The method for culturing cells according to claim 6, further comprising:
subjecting the cell suspension extracted from the culture vessel to a separation treatment by which the extracted cell suspension is separated, by using a separation membrane, into a first solution having a cell concentration higher than a cell concentration in the cell suspension and a second solution having a cell concentration lower than the cell concentration in the cell suspension by a tangential flow filtration method,
returning the first solution to the culture vessel; and
adding a medium anew to the culture vessel.

13. A method for producing a product, comprising:
culturing cells that produce a product, using the method for culturing cells according to claim 6; and
recovering the product from a cell suspension of the cells.

14. The method for producing a product according to claim 13,
wherein the product is an antibody.

\* \* \* \* \*